(12) United States Patent
Prince

(10) Patent No.: US 6,662,038 B2
(45) Date of Patent: *Dec. 9, 2003

(54) METHOD AND APPARATUS FOR IMAGING ABDOMINAL AORTA AND AORTIC ANEURYSMS

(76) Inventor: Martin R. Prince, 2022 Delafield St., Ann Arbor, MI (US) 48105

( * ) Notice: Subject to any disclaimer, the term of this patent is extended or adjusted under 35 U.S.C. 154(b) by 40 days.

This patent is subject to a terminal disclaimer.

(21) Appl. No.: 09/828,428

(22) Filed: Apr. 7, 2001

(65) Prior Publication Data

US 2001/0027265 A1 Oct. 4, 2001

Related U.S. Application Data

(63) Continuation of application No. 09/124,262, filed on Jul. 29, 1998, now Pat. No. 6,230,041, which is a continuation of application No. 08/715,736, filed on Sep. 19, 1996, now Pat. No. 5,799,649, which is a continuation of application No. 08/420,815, filed on Apr. 12, 1995, now Pat. No. 5,579,767, which is a continuation-in-part of application No. 08/378,384, filed on Jan. 25, 1995, now Pat. No. 5,553,619, which is a continuation-in-part of application No. 08/071,970, filed on Jun. 7, 1993, now Pat. No. 5,417,213.

(51) Int. Cl.$^7$ .............................................. A61B 5/055
(52) U.S. Cl. ...................... 600/420; 600/410; 600/419; 324/307; 324/309; 382/130
(58) Field of Search ................... 600/410, 419, 600/420; 324/306, 307, 309; 382/130

(56) References Cited

U.S. PATENT DOCUMENTS

| | | |
|---|---|---|
| 3,973,554 A | 8/1976 | Tipton |
| 4,006,736 A | 2/1977 | Kranys et al. |
| 4,202,333 A | 5/1980 | Thill et al. |

(List continued on next page.)

FOREIGN PATENT DOCUMENTS

EP 0 543 468 5/1993

OTHER PUBLICATIONS

"Normal abdominal enhancement patterns with dynamic gadolinium–enhanced MR imaging", Mirowitz, et al., Radiology, vl.180, No. 3, Sep. 1, 1991, p. 637–640, XP000577881.

"Contrast enhancement in abdominal CT Bolus vs. Infusion", Bergener, et al., American Journal of Roentgenology, v.137, Aug. 1, 1981, p. 351–358, XP000577961.

"Clinical application of pulmonary 3 dimensional time–of–flight MR angiography with breath–holding using a contrast medium", Isoda, et al., Society of Magnetic Resonance in Medicine, 11th Annual Scientific Meeting, Aug. 8–14, 1992, Berlin, Germany, Works in Progress, p. 3119, XP00211479.

(List continued on next page.)

Primary Examiner—George Manuel
Assistant Examiner—Barry Pass
(74) Attorney, Agent, or Firm—Neil Steinberg

(57) ABSTRACT

The present invention is a technique and apparatus for acquiring anatomic information used in diagnosing and characterizing abdominal aortic aneurismal disease and the like. This technique provides anatomic information, in the form of images, using a combination of a plurality of magnetic resonance angiography sequences, including a spin-echo and four contrast enhanced (e.g., gadolinium) magnetic resonance angiography sequences. The anatomic images may be used in, for example, pre-operative, operative and post-operative evaluation of aortic pathology, including aneurysms, atherosclerosis, and occlusive disease of branch vessels such as the renal arteries. The gadolinium-enhanced magnetic resonance angiography provides sufficient anatomic detail to detect aneurysms and all relevant major branch vessel abnormalities seen at angiography operation. This technique and apparatus allows for imaging the aorta at a fraction of the cost of conventional aortography and without the risks of arterial catheterization or iodinated contrast.

45 Claims, 9 Drawing Sheets

U.S. PATENT DOCUMENTS

| | | |
|---|---|---|
| 4,298,000 A | 11/1981 | Thill et al. |
| 4,430,079 A | 2/1984 | Thill et al. |
| 4,585,008 A | 4/1986 | Jarkewicz |
| 4,585,941 A | 4/1986 | Bergner |
| 4,597,754 A | 7/1986 | Thill et al. |
| 4,718,424 A | 1/1988 | Nishimura |
| 4,770,183 A | 9/1988 | Groman et al. |
| 4,777,957 A | 10/1988 | Wehroli et al. |
| 4,822,594 A | 4/1989 | Gibby |
| 4,826,673 A | 5/1989 | Dean et al. |
| 4,865,043 A | 9/1989 | Shimoni |
| 4,877,599 A | 10/1989 | Lees |
| 4,880,008 A | 11/1989 | Lauffer |
| 4,915,111 A | 4/1990 | Sano et al. |
| 5,010,191 A | 4/1991 | Engelstad et al. |
| 5,011,686 A | 4/1991 | Pang |
| 5,034,694 A | 7/1991 | Sattin et al. |
| 5,055,288 A | 10/1991 | Lewis et al. |
| 5,078,986 A | 1/1992 | Bosworth et al. |
| 5,087,439 A | 2/1992 | Quay |
| 5,141,740 A | 8/1992 | Rajagopalan et al. |
| 5,167,232 A | 12/1992 | Parker et al. |
| 5,190,744 A | 3/1993 | Rocklage et al. |
| 5,243,284 A | 9/1993 | Noll |
| 5,260,050 A | 11/1993 | Ranney |
| 5,287,273 A | 2/1994 | Kupfer et al. ............... 600/420 |
| 5,305,751 A | 4/1994 | Chopp et al. |
| 5,315,997 A | 5/1994 | Widder et al. |
| 5,341,099 A | 8/1994 | Suzuki |
| 5,451,211 A | 9/1995 | Neer et al. |
| 5,494,036 A | 2/1996 | Uber, III et al. |
| 5,515,863 A | 5/1996 | Damadian ................... 600/420 |
| 5,522,390 A | 6/1996 | Tuithof et al. ............... 600/420 |
| 5,792,056 A | 8/1998 | Prince ......................... 600/420 |
| 5,799,649 A | 9/1998 | Prince ......................... 600/420 |

OTHER PUBLICATIONS

"The arterial concentration of Gd–DTPA can be monitored non–invasively", Soodergaard, et al., Society of Magnetic Resonance in Medicine, 11th Annual Scientific Meeting, Aug. 8–14, 1992, Berlin, Germany, Book of Abstracts, v.1, p. 1120, XP002111480.

"Fast–scan magnetic resonance: Principles and applications", Wehrli, Magnetic Resonance Quarterly, v.6, No. 3, 1990, p. 165–236, XP002111477.

A Rapid Interleaved Method for Measuring Signal Intensity Curves in both Blood and Tissue during Contrast Agent Administration, Taylor et al., Magnetic Resonance In Medicine, 30, 1993, pp. 744–749.

"Cerebrovascular Magnetic Resonance Angiography", Wesbey et al., J. Vascular Surgery 1992, vol. 16, No. 4, pp. 619–632.

"Volume MR Angiography: Methods to Achieve Very Short Echo Times", Schmalbrock et al., Radiology 1990, vol. 175, pp. 861–865.

"Three Dimension (Volume) Gradient–Echo Imaging of the Carotid Bifurcation: Preliminary Clinical Experience", Masaryk et al., Radiology 1989, vol. 171, pp. 801–806.

"Gadolinium–enhanced Magnitude Contrast MR Angiography of Popliteal and Tibial Arteries", Lossef et al., Radiology 1989, vol. 184, pp. 349–355.

"Intercranial Circulation: Preliminary Clinical Results with Three–Dimensional (Volume) MR Angiography", Masaryk et al., Radiology 1989, vol. 171, pp. 793–799.

"Abdominal Aorta and Renal Artery Stenosis: Evaluation with MR Angiography", Kim, et al.,Radiology, vol. 174, pp. 727–731, Mar. 1990.

"Intercranial Vascular Lesions: Optimization and Clinical Evaluation of Three–Dimensional Time–of–Flight MR Angiography", Marchal, et al., Radiology, vol. 175, pp. 443–448, May 1990.

"Normal Venous Anatomy of the Brain: Demonstration with Gadopentatate Dimeglumine in Enhanced 3–D MR Angiography", Chakeres, et al., AJR, vol. 156, pp. 161–172, Jan. 1991.

"Three–dimensional Time–of–Flight MR Angiography: Applications in the Abdomen and Thorax", Lewin, et al., Radiology, vol. 179, No. 1, pp. 261–264, Apr. 1991.

"Safety of Gadolinium–DPTA: Extended Clinical Experience", Niendorf, et al., SMRM Workshop on Contrast Enhanced Magnetic Resonance, May 23–25, 1991.

"Fast Time–of–Flight MR Angiography with Improved Background Suppression", Edelman, et al, Radiology, vol. 179, pp. 867–870, Jun. 1991.

"Assessment of Carotid Artery Stenosis by MR Angiography: Comparison with X–ray Angiography and Color Coded Doppler Ultrasound", Anderson, et al., AJNR, vol. 13, pp. 989–1003, May/Jun. 1992.

"Gadolinium–enhanced High–Resolution MR Angiography with Adaptive Vessel Tracking: Preliminary Result in the Intercranial Circulation", Lin, et al, JMRI, vol. 2, pp. 277–284, May/Jun. 1992.

"Experience with High–Dose Gadolinium MR Imaging in the Evaluation of Brain Metastases", Yuh, et al., AJNR, vol. 13, pp. 335–345, Jan./Feb. 1992.

"Frequency Dependence of Tissue Relaxation Times", Bottomly.

"Abdominal Aortography with Dynamic High–Dose Gadopentetate Dimeglumine", Prince, SMRM 12th Annual Meeting, Aug., 1993.

"Dynamic Gadolinium–Enhanced Three–dimensional Abdominal MR Arteriography", Prince et al.,JMRI, vol. 3, No. 6 Nov./Dec. 1993.

"Gadolinium–enhanced MR Aortography", Prince, Radiology, vol. 191, No. 1,pp. 155–164, Apr. 1994.

"Optimizing Blood Vessel Contrast in Fast Three–Dimensional MRI", Haacke, et al., SMRM Workshop on MR Imaging of Blood Flow, Mar. 13–14, 1989.

"Magnetic Resonance Angiography of the Thoracic Aorta", Prince, et al., Magnetic Resonance Angiography: A Practical Approach, Chapter 10, pp. 131–138.

"Contrast Enhancement in Abdominal CT: Bolus vs. Infusion", Burgener, et al., AJR, vol. 137, pp. 351–358, 1981.

"MRA Adds Value in Body Imaging", Prince, MR, vol. 5, No. 3, pp. 29–31, Summer 1995.

"3D–MR–Angiographie mit Gd–DTPA", Seiderer, et al., Fortschr. Rontgenstr., 152–153 (1990), pp. 327–332.

"Fast Magnetic Resonance Angiography Using Turbo–FLASH Sequences in Advanced Aortoiliac Disease", Sivananthan, et al., The British Journal of Radiology, vol. 66, No. 792, pp. 1103–1110, Dec. 1993.

"Contrast–Enhanced Magnetic Resonance Tomoangiography: A New Imaging Technique for Studying Thoracic Great Vessels", Revel, et al., Magnetic Resonance Imaging, vol. 11, pp. 1101–1105, Nov. 8, 1993.

"MR Imaging (Including MR Angiography) of Adbominal Aortic Aneurysms: Comparison with Conventional Angiography", Kaufman, et al., AJR, 163, pp. 203–210, Jul. 1994.

"Gadolinium–Enhanced MR Aortography", Prince, Radiology, p. 193, Nov. 1994.

"Magnetic Resonance Angiography of the Renal and Visceral Arteries", Kaufman, et al., Magnetic Resonance Angiography: A Practial Approach, Chapter 12, pp. 161–170.

"Gadolinium–Enhanced Magnetic Resonance Angiography of Abdominal Aortic Aneurysms", Prince, et al., Journal of Vascular Surgery, vol. 21, No. 4, pp. 656–669, Apr. 1995.

"Breath–Hold Gadolinium–Enhanced MR Angiography of the Abdominal Aorta and its Major Branches", Prince, et al., Radiology, vol. 197, No. 3, pp. 785–792, Dec. 1995.

"Gadolinium Enhanced MR Imaging of Vascular Stents", Matsumoto et al., Journal of Computer Assisted Tomography, vol. 14, No. 3, pp. 357–361, May/Jun. 1990.

Magnetic Resonance Angiography, Concepts & Applications, Potchen et al., chapter 16, Magnetopharmaceuticals as contrasts agents, Marchal et al., pp. 305–322, 1993.

"Evaluation of Renal Artery Stenosis with Dynamic Gadolinium–Enhanced MR Angiography: Work in Progress", Rieumont, et al., Radiology, p. 193, Nov. 1994.

"An Extended–Length Coil Design for Peripheral MR Angiography", Rajan et al., Magnetic Resonance Imaging, vol. 9, No. 4, pp. 493–495, 1991.

"Fast MRI with turbo–Flash Sequences in Aortoiliac Disease", Sivanathan et al., The Lancet, vol. 338, pp. 1090–1091, Oct. 26, 1991.

"The Use of Contrast–Enhanced TurboFLASH Sequences in Aorto–Iliac Disease and Their Comparison with Conventional Angiography", Sivanathan et al., SMRM 1992, Berlin, p. 3108.

"Preliminary Study of Pulmonary Three–Dimesional Time of Flight MR Angiography with Breath–Holding Using a Contrast Medium", Isoda et al., Radiation Medicine, vol. 11, No. 5, Sep.–Oct. 1993, pp. 191–195.

"Fast Three–Dimensional Time–of–Flight MR Angiography with Timed Injection of Contrast Material", Kanal et al., Radiology 1991; vol. 181(P), 119 (abstract 169C).

"Fast Three–Dimensional Time–of–Flight MR Angiography with Contrast Bolus Injection", Talagala et al., SMRI 1992, paper #332.

"Fast RF–spoiled Three–dimensional MR Angiography of Intracranial Vasculature in Scan Times under 1 minute", Talagala et al., Book of Abstracts, SMRM 1991, p. 1021.

"A Perspective on K–Space", Mezrich, Radiology, vol. 195, No. 2, 1995, p. 297–315.

FIG.8A  Pre Gado
FIG.8B  During Gado Infusion
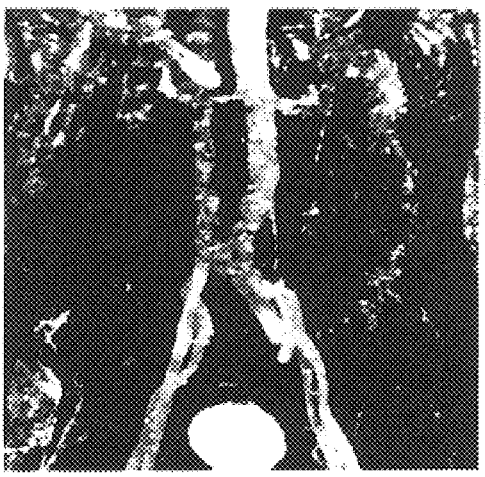
FIG.8C  Post Gado

METHOD AND APPARATUS FOR IMAGING ABDOMINAL AORTA AND AORTIC ANEURYSMS

This application is a continuation of application Ser. No. 09/124,262, filed on Jul. 29, 1998 now U.S. Pat. No. 6,230,041, which is a continuation of application Ser. No. 08/715,736, filed on Sep. 19, 1996 now U.S. Pat. No. 5,799,649, which is a continuation of application Ser. No. 08/420,815, filed on Apr. 12, 1995, now U.S. Pat. No. 5,579,767, which is a continuation-in-part of application Ser. No. 08/378,384, filed on Jan. 25, 1995, now U.S. Pat. No. 5,553,619; which is a continuation-in-part of application Ser. No. 08/071,970, filed on Jun. 7, 1993, now U.S. Pat. No. 5,417,213.

It is hereby noted that work associated with reducing this invention to practice was supported, in part, by the National Institutes of Health, under Grant No. HL 46384. The United States Government may have certain rights in this invention.

BACKGROUND OF THE INVENTION

This invention relates to a method of, and apparatus for use in, magnetic resonance imaging; and more particularly, to contrast agent enhanced magnetic resonance angiography for examining, detecting, diagnosing, and treating arterial diseases and injuries, including defining anatomic features relevant to performing aorta and aortic surgery for aneurysmal disease.

Arterial diseases and injuries are common and often have severe consequences including death. Imaging arteries serves to detect and characterize arterial disease before these consequences occur as well as defining anatomic features to assist in performing surgery for aneurysmal disease.

A conventional method of arterial imaging includes inserting a catheter into the artery of interest (the artery under study) and injecting radiographic contrast, for example, an iodinated contrast, while taking radiographs of the artery. Radiographs are commonly referred to as X-rays. In this technique, the contrast remains in the arteries for a few seconds during which the arteries appear distinct from both the veins and background tissue in the radiographs.

Although a catheter-based contrast arteriography technique generally provides high quality arterial images, there is a risk of arterial injury or damage by the catheter and its insertion. There may be thrombosis, dissection, embolization, perforation or other injury to the artery itself. Furthermore, such a technique may result in a stroke, loss of a limb, infarction or other injury to the tissue supplied by the artery. In addition, hemorrhage at the catheter insertion or perforation sites may require blood transfusions. Moreover, kidney failure and brain injury may result from the toxic effects of the X-ray contrast.

More recent techniques of arterial imaging are based upon detecting the motion of the blood within the arteries and/or veins.

These techniques involve employing magnetic resonance imaging (MRI) to image moving blood distinct from stationary background tissues. (See, e.g., Potchen, et al., eds., "Magnetic Resonance Angiography/Concepts and Applications", Mosby, St. Louis, 1993; the text of which is incorporated herein by reference). Such techniques do not necessitate catheter insertion into the artery. These techniques are commonly known as 2D time-of-flight, 3D time-of-flight, MOTSA, magnitude contrast, phase contrast, and spin echo black blood imaging.

With pre-saturation pulses it is possible to primarily image blood flowing in one direction. Since arteries and veins generally flow in opposite directions, these pre-saturation pulses allow preferential visualization of the arteries or the veins. Because these techniques depend upon blood motion, the images are degraded in patients who have arterial diseases which decrease or disturb normal blood flow. Such types of arterial diseases that decrease or disturb normal blood flow include aneurysms, arterial stenoses, arterial occlusions, low cardiac output and others. The resulting lack of normal blood flow is particularly problematic because it is those patients with disturbed blood flow in whom it is most important to acquire good quality arterial images.

A related MRI technique relies on differences in the proton relaxation properties between blood and background tissues. (See, e.g., Marchal, et al., in Potchen, et al., eds., supra, pp. 305–322). This technique does not depend upon steady blood in-flow. Instead, this MRI technique involves directly imaging the arteries after administering a paramagnetic contrast agent. Here, after administering the contrast agent, it is possible to image arteries directly based upon the blood relaxation properties. This technique overcomes many of the flow related problems associated with MRI techniques which depend upon blood motion.

Several experts have performed magnetic resonance arterial imaging using intravenous injection of gadolinium chelates (paramagnetic contrast agents). These experts have reported their results and conclusions. In short, these results have been disappointing and, as a result, the use of gadolinium for imaging arteries has not been adopted or embraced as a viable arterial imaging technique. The images using this technique are difficult to interpret because the gadolinium tends to enhance both the arteries and the veins. Since the arteries and veins are closely intertwined, it is extremely difficult to adequately evaluate the arteries when the veins are visible. Further, the difficulty in interpretation is exacerbated as a result of contrast leakage into the background tissues.

However, MRI has evolved over the past decade to become an accepted technique to image the abdominal aorta and abdominal aortic aneurysms. Advances in magnetic resonance imaging for vascular imaging, known as magnetic resonance angiography, have enabled the additional evaluation of aortic branch vessels. However, limitations in magnetic resonance angiography imaging of the slow, swirling flow within aneurysms, turbulent flow in stenoses, and tortuous iliac arteries have limited the usefulness of these general studies in providing detailed information necessary for preoperative planning. In spite of these limitations, recent developments in gadolinium-enhanced magnetic resonance angiography have overcome several of the imaging problems. (See, e.g., Debatin et al., "Renal magnetic resonance angiography in the preoperative detection of supernumerary renal arteries in potential kidney donors", Invest. Radiol. 1993;28:882–889; Prince et al., "Dynamic gadolinium-enhanced three-dimensional abdominal MR arteriography", JMRI 1993;3:877–881; and Prince, "Gadolinium-Enhanced MR Aortography", Radiology 1994;191(1):155–64).

There exists a need for an improved method of magnetic resonance angiography which provides an image of the arteries distinct from the veins and which overcomes the limitations of other techniques. Further, there exists a need for an apparatus which facilitates providing an image of the arteries distinct from the veins and which may be implemented in overcoming the limitations of other techniques.

Moreover, these exists a need for contrast (e.g., gadolinium) enhanced magnetic resonance angiography of abdominal aortic aneurysms to provide essential and accurate anatomic information for aortic reconstructive surgery devoid of contrast-related renal toxicity or catheterization-related complications attending conventional arteriography.

SUMMARY OF THE INVENTION

In one aspect, the present invention is a method of imaging an aorta and aortic aneurysm of a patient using magnetic resonance imaging. The method includes performing a first imaging sequence to identify the location of the aneurysm and performing a second imaging sequence to image the aorta and extent of the aortic aneurysm. The second imaging sequence includes collecting image data and administering magnetic resonance contrast agent to the patient prior to and/or while collecting image data, by intravenous infusion, at a rate of infusion sufficient to provide a substantially elevated concentration of the contrast agent in the artery during collection of image data representative of a center of k-space.

The first imaging sequence may be a sagittal T1 weighted sequence. The second imaging sequence may be a plurality of images constructed from a dynamic 3D volume. The plurality of images of the second imaging sequence may include a plurality of coronal, sagittal or oblique projections.

The method may further include the step of performing at least a third imaging sequence for imaging the size of the aortic aneurysm. The third imaging sequence may be performed after performing the second imaging sequence. In a preferred embodiment, the third imaging sequence is a plurality of sagittal or axial 2D time-of-flight images and further includes collecting imaging data while the patient suspends respiration.

In another preferred embodiment, the method includes the step of performing a fourth imaging sequence for imaging the size of the aortic aneurysm wherein the third and fourth imaging sequences are a plurality of sagittal and axial 2D time-of-flight images.

In yet another preferred embodiment, the invention includes performing a fifth imaging sequence for imaging right renal arteries. The fifth imaging sequence may include collecting data representative of phase contrast images.

In another aspect, the invention is a method of imaging portions of the aorta and its major branches in a patient using magnetic resonance imaging. The method includes performing a first imaging sequence to identify the location of the aorta and performing a second imaging sequence to image a lumen of the aorta. The second imaging sequence includes collecting image data representative of the center of k-space while the patient suspends respiration. The second imaging sequence further includes administering magnetic resonance contrast agent to the patient, by intravenous infusion, at a rate of infusion sufficient to provide a substantially elevated concentration of the contrast agent in the artery during collection of image data representative of a center of k-space.

In a preferred embodiment, the first imaging sequence is a sagittal T1 weighted sequence. In another preferred embodiment, the second imaging sequence is a 3D gradient echo volume.

In another preferred embodiment, the method includes a third imaging sequence, following the step of administering magnetic resonance contrast agent, for collecting 3D phase contrast images.

In yet another aspect, the present invention is a method of imaging aorta or renal arteries of a patient using magnetic resonance imaging. The method includes performing a first imaging sequence to identify the location of the aorta and aorta branch vessels and performing a second imaging sequence to image a lumen of the aorta. The second imaging sequence includes collecting image data and administering magnetic resonance contrast agent to the patient prior to or while collecting image data, by intravenous infusion, at a rate of infusion sufficient to provide a substantially elevated concentration of the contrast agent in the artery during collection of image data representative of a center of k-space.

The step of performing the second imaging sequence may include collecting at least a portion of the image data while the patient suspends respiration. In a preferred embodiment, the step of performing the second imaging sequence includes collecting at least a portion of the image data corresponding to the center of k-space while the patient suspends respiration.

The present invention overcomes the limitations of other techniques by injecting magnetic resonance contrast agents at a sufficient rate, at a selected time relative to the collection of image data, and for an appropriate duration in such a manner that the contrast level in the arteries is higher than that in surrounding veins and background tissue during collection of image data. The injection may be intravenously in a vein remote from the artery of interest. Intravenous injection eliminates the risks associated with arterial catheterization. In the present invention, the high level of arterial contrast permits directly imaging the arterial lumen, analogous to conventional arteriography. Moreover, using a magnetic resonance pulse sequence which is not as sensitive to motion and by relying on image contrast related to differences in T1 relaxation rather than the in-flow effect, a reduction in the flow artifacts associated with phase contrast or magnitude contrast (time-of-flight) magnetic resonance angiography is observed.

In short, the present invention is, in comparison or relative to other techniques, a method of magnetic resonance angiography which combines several of the advantages of catheter-based contrast arteriography with the advantages of magnetic resonance imaging while substantially eliminating the disadvantages of each.

BRIEF DESCRIPTION OF THE DRAWINGS

In the course of the detailed description of preferred embodiments to follow, reference will be made to the attached drawings, in which:

FIGS. 8A–C illustrate typical coronal maximum intensity projection (MIP) collapse images obtained (FIG. 8A) prior to injection of gadopentetate dimeglumine, (FIG. 8B) dynamically during intravenous injection of gadopentetate dimeglumine, 0.2 millimoles/kilogram over 5 minutes, and (FIG. 8C) immediately following injection of gadopentetate dimeglumine;

DETAILED DESCRIPTION

Figure 1:
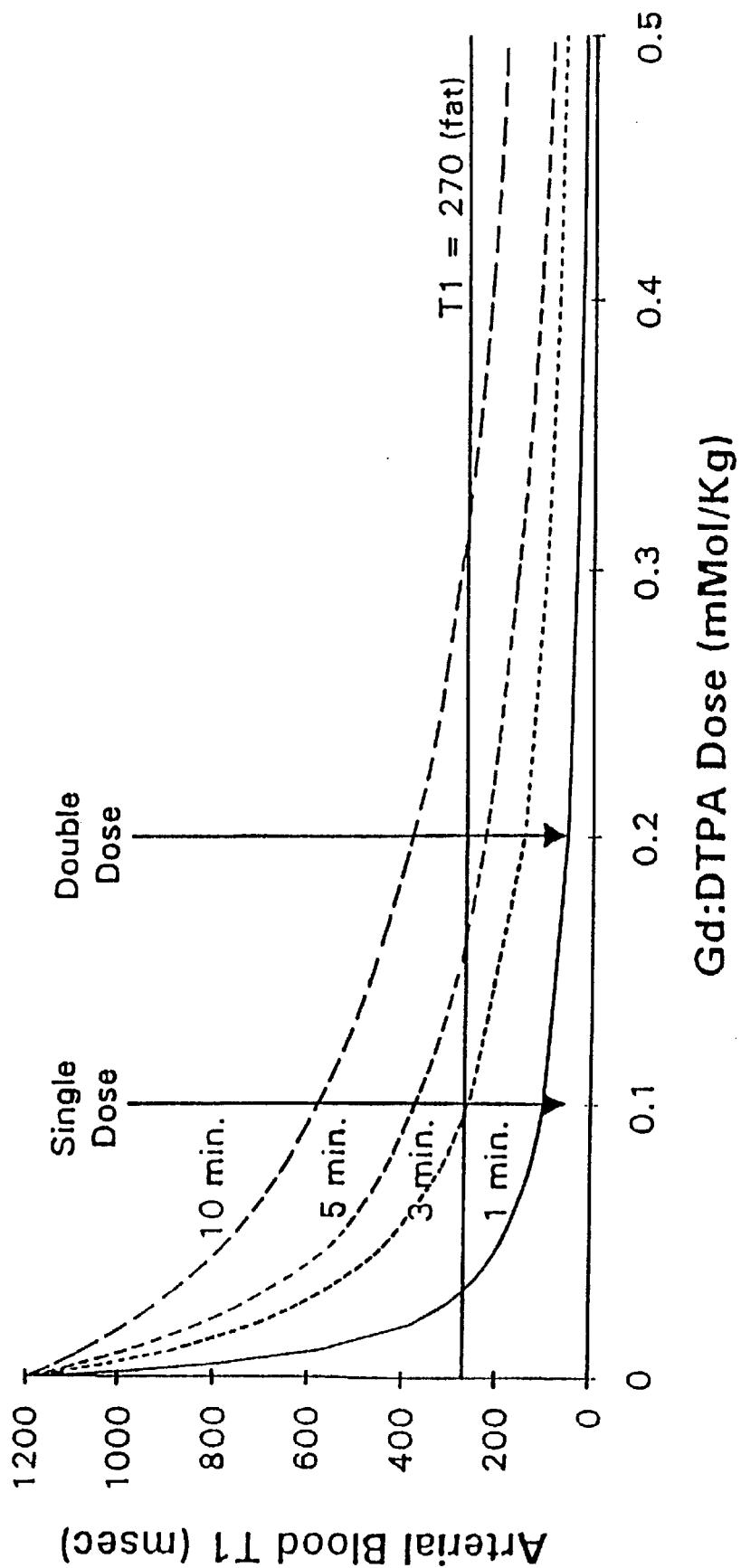
FIG. 1 illustrates longitudinal relaxation time (T1) of blood as a function of injection imaging time and total paramagnetic contrast dose for a compound with a relaxivity of 4.5/millimolar-second.

The present invention is a technique and apparatus for acquiring anatomic information used in characterizing and/or evaluating abdominal aortic aneurysmal disease and the like. This technique provides anatomic information, in the form of images, by using a combination of a plurality of magnetic resonance angiography sequences, including one spin-echo and four magnetic resonance agent (e.g., gadolinium) enhanced magnetic resonance angiography sequences. The anatomic images may be used in, for example, pre-operative, operative and post-operative evaluation of abdominal aortic aneurysms and/or abdominal aortic aneurysm surgery. The gadolinium-enhanced magnetic resonance angiography provides sufficient anatomic detail to detect aneurysms and all relevant major branch vessel abnormalities seen at angiography pr is at operation.

Briefly, by way of overview, an evaluation of abdominal aortic aneurysms may require one, some or all of the following magnetic resonance image sequences:

(1) an initial weighted T1 sequence; the T1 sequence may be used to identify the location of the aneurysm. This sequence may also be employed to define the location of renal and splanchnic arteries for planning higher resolution gadolinium-enhanced sequences (discussed below). Further, the T1 sequence may provide information as to the approximate size of each kidney, the size of the aneurysm, and the location of the left renal vein. A preferred orientation of this sequence is in the sagittal plane;

(2) a dynamic gadolinium-enhanced 3D volume sequence; the 3D volume sequence may be obtained in the coronal plane and reconstructed into sagittal, axial and/or oblique projections to produce images that are similar to biplane aortography or helical CT angiography. In a preferred embodiment, these images are employed to evaluate the renal and splanchnic artery origins, the iliac arteries, and the distal extent of the aneurysm;

(3&4) sagittal and axial 2D time-of-flight images; the sagittal and axial 2D time-of-flight images demonstrate the maximum size of the aneurysm, its proximal extent and peri-aneurysm inflammation. The sagittal and axial 2D time-of-flight images may be employed to detect the presence of thrombus and the features of the thrombus, including its location, surface irregularity and/or enhancement; and (5) 3D phase contrast images; the 3D phase contrast volume images defines the renal arteries in greater detail to facilitate grading the severity of occlusive lesions.

In addition, in one embodiment of the present invention, a combination of gadolinium-enhanced magnetic resonance angiographic sequences are used to provide a highly accurate mechanism for detecting, examining and grading occlusive lesions. Such information is valuable during many stages of evaluation of the patients.

Moreover, although information relating to thrombus is not important for conventional abdominal aortic aneurysm operations, assessment of intraluminal thrombus may be significant when planning endoluminal stent graft placement, as the latter technology is introduced into clinical practice. The thrombus may be detected from the sagittal and axial 2D time-of-flight images. These images may also be used to identify the features of the thrombus, including its location, surface character, and/or enhancement. Such information may be used to determine the embolic potential of the thrombus. Furthermore, the axial and sagittal images facilitate in accurately ascertaining aorta diameter and length which may facilitate customization of an endoluminal graft for a given abdominal aortic aneurysm.

EXAMPLE 5, set forth in detail below, defines the imaging parameters of the magnetic resonance image sequences (initial sagittal T1 sequence, dynamic gadolinium-enhanced 3D volume sequence, sagittal and axial 2D time-of-flight images, and 3D phase contrast images).

The sequence outlined above may be employed in different combinations for providing anatomic images of the abdominal aorta. Under some circumstances when imaging abdominal aortic aneurysms, not all of sequences are necessary. An imaging technique using one or several of the sequences may provide limited information of, for example, the distal end of the aneurysm (dynamic gadolinium enhanced 3D volume imaging sequence) and the maximum size of the aneurysm (sagittal and axial 2D time-of-flight images). One skilled in the art would recognize that other permutations of the sequences are possible and the number and combination of the sequences may be tailored according to the information needed or desired.

Further, several of the sequences may be repeated in order to collect additional, but somewhat redundant information. A sequence may be performed more than once in order to check the imaging results which are obtained from other sequences. Thus, in short, numerous permutations of sequences may be implemented to provide varying degrees of evaluation, as well as certainty, of abdominal aortic aneurysms. A combination of these sequences may be used to evaluate patients suspected of having other pathology, such as renal artery stenosis or mesenteric ischemia.

The magnetic resonance angiography sequences of the present invention may be performed during or following infusion of magnetic resonance contrast agent (e.g., gadolinium). Under this circumstance, these sequences may provide preferential enhancement of an artery of interest relative to adjacent veins and background tissue by adapting the timing of a maximum or substantially elevated rate of infusion to correlate with the collection of image data representative of the center of k-space. In this technique one or more of the magnetic resonance angiography sequences may be temporally correlated with the timing of a maximum or substantially elevated rate of infusion of contrast and the mapping of k-space according to the location of the artery of interest, the size of the artery of interest, the physical condition of the patient, the time delay due to the configuration of the contrast agent delivery system, and/or the type of pulse sequence employed by the imaging apparatus. Adapting the timing of a maximum or substantially elevated rate of infusion to correlate with the collection of image data corresponding to the center of k-space provides a period of a maximum or substantially elevated contrast concentration in the artery of interest relative to adjacent veins during collection of at least a portion of the image data representative of the center of k-space.

In particular, in one aspect of the present invention, the contrast agent enhanced magnetic resonance angiography sequences generate imaging data over a period of simultaneous controlled intravenous injection of a magnetic resonance contrast agent. The magnetic resonance contrast agent is preferably injected into a patient, for example, a human or other animal, substantially throughout the period of imaging in a controlled manner, i.e., injected at a controlled rate over the period of imaging. In one embodiment, the magnetic resonance contrast agent is administered as a steady and continuous infusion in a vein which is remote from the artery of interest (i.e., the artery under study).

Magnetic resonance contrast agents employed in the present invention are well known in the art, and are disclosed in, for example, U.S. Pat. Nos. 5,141,740; 5,078,986; 5,055,288; 5,010,191; 4,826,673; 4,822,594; and 4,770,183, which are incorporated herein by reference. Such magnetic resonance contrast agents include many different paramagnetic contrast agents, for example, gadolinium compounds. Gadopentetate dimeglumine, gadodiamide and gadoteridol are paramagnetic gadolinium chelates that are readily available, and which rapidly redistribute into the extracellular fluid compartment. Other gadolinium compounds are acceptable, and may have a higher relaxivity, more rapid redistribution into the extracellular fluid compartment, and greater and faster extraction in the capillary bed. It should be noted that, contrast agents that are extracted or degrade in or near the capillary bed are preferred for the present invention.

In one preferred embodiment, when performing at least one of the magnetic resonance angiography sequences, the injected contrast agent should be sufficiently small to rapidly redistribute into the extracellular fluid compartment in the systemic capillary bed, or the contrast agent should be actively extracted from the circulation in the capillary bed distal to the artery of interest, or both. Under these circumstances, the artery (or arteries) of interest contains a high concentration of contrast and the vein (or veins) adjacent to the artery (or arteries) of interest possesses a lower contrast concentration. Further, under these circumstances, the relationship of artery-to-venous contrast concentration is substantially maintained over the period of contrast injection.

By matching the duration of the injection when performing at least one of the magnetic resonance angiography sequences with the time required for a longitudinal relaxation time (T1) weighted magnetic resonance image data set, it is possible to view the arteries distinct from the veins. Further, by injecting the contrast at a sufficient rate, the longitudinal relaxation time of the arterial blood may be made sufficiently short when compared to that of the background tissues. As a result, the image of the arteries is distinct from background tissue as well.

As mentioned above, the magnetic resonance contrast agent is administered to the patient, for example, a human or other animal, via intravenous infusion, i.e., injection into a patient at a controlled rate over a period of time. In a preferred embodiment, the period of infusion of magnetic resonance contrast agent may be a substantial portion of the time during which image data is being collected for a magnetic resonance image. A substantial portion of the data collection time is a majority of the time and should include the period of time during which the center of k-space is acquired.

In another preferred embodiment, when executing the magnetic resonance angiography sequences, a maximum or elevated rate of infusion is correlated with collecting of image data representing the center of k-space. That is, a maximum or elevated rate of injection of contrast is timed so that the maximum arterial contrast concentration occurs while mapping the center of k-space. The center of k-space refers to the low spatial frequency MR image data. In a preferred embodiment, the timing of the infusion of the magnetic resonance contrast agent (e.g., gadolinium), however, is compensated to account for the time which may be necessary for the contrast agent to circulate from the site of injection, through the heart and lungs, and into the artery of interest. Under this circumstance, in order to more accurately correlate a maximum or elevated rate of infusion of the contrast agent with collection of image data representative of the center of k-space, it may be necessary for the period of a maximum or substantially elevated rate of infusion of contrast to be forwardly shifted in time relative to the acquisition or collection of image data representing the center of k-space.

Correlating the maximum or substantially elevated rate of infusion with the mapping of k-space accounts for the time delay due to the contrast agent delivery system (e.g., the length of catheter which delivers the contrast agent) and/or the time-delay due to the time required for the gadolinium to circulate from the site of injection, through the body, and into the artery of at interest. Further, correlating a maximum or elevated rate of infusion with the mapping of the center of k-space provides for a period of maximum or elevated arterial contrast in the artery of interest to occur during collection of image data corresponding to the center of k-space (which in most pulse sequences is collected during the middle of a scan).

Typically, there is a delay of about 10–50 seconds from the time of administering the contrast agent at a maximum or substantially elevated rate to the realization of a maximum or elevated arterial contrast in the artery of interest relative to adjacent veins. As a result, the amount of time necessary to align the collection of data representing the center of k-space with a period of maximum or elevated arterial contrast is about 10 to 50 seconds after initiating maximum or substantially elevated rate of infusion. That is, the maximum or substantially elevated rate of infusion should occur about 10 to 40 seconds prior to acquiring image data representative of the center of center of k-space to "compensate" for the contrast delivery system and the circulation time of the contrast agent. In this regard, the maximum rate of infusion of the contrast agent is correlated with the collection of image data which corresponds to the center of k-space in that a period of maximum or elevated arterial contrast occurs during the mapping of the center of k-space.

In some instances during performance of the magnetic resonance angiography, the pulse sequence of the imaging apparatus may be designed such that data representing the center of k-space is collected at the beginning of a scan. Under this circumstance, the above described technique may be implemented by injecting contrast agent prior to the image scanning process (collection of image data) so that the injection of the contrast agent is properly correlated to the acquisition of data corresponding to the center of k-space and a period of maximum or elevated arterial contrast coincides with that data acquisition.

In one preferred embodiment, the timing of the infusion of the contrast agent may be further adjusted according to the physical condition of the patient. That is, the timing of the administration of the contrast agent to, for example, correlate a maximum or elevated rate of infusion with the mapping of k-space, may be adjusted according to a patient's physical condition which may affect the amount of time for contrast to circulate from the site of infusion (typically an arm vein) to the artery of interest. Although this time interval will typically be about 10–40 seconds, patients with cardiac disease or under sedation may have a slower flow, which may suggest a time interval of about 30 seconds or greater.

In contrast, young healthy patients, and especially patients who have recently exercised, will have a faster flow, which may suggest a time interval of less than 20 seconds. Faster flow is also seen in patients with arterio-venous fistulas. The circulation time will also be decreased in patients who have central lines that allow injection of contrast close to or directly into the heart.

In another preferred embodiment, the timing of a maximum or substantially elevated infusion rate may be further selected or controlled, based on the location of the artery of interest relative to the injection site and/or the patient's heart, to provide a period of maximum or elevated arterial contrast concentration in the artery of interest relative to adjacent veins during collection of image data which corresponds to the center of k-space. In this regard, the amount of time between a maximum or elevated rate of injection and a maximum or elevated arterial contrast is realized in the artery of interest may be longer if the artery of interest is far from the heart, for example, in the foot, or if the site of infusion is a peripheral vein such as in the hand. Thus, in this preferred embodiment, the correlation of the maximum rate of injection with the collection of image data representative of the center of k-space includes adapting the time between the maximum rate of injection and the mapping of the center of k-space to reflect the relative location of the artery of interest.

In another preferred embodiment of performing the magnetic resonance angiography sequences, the correlation between a maximum or elevated rate of injection and the collection of image data representative of the center of k-space may be adjusted or controlled in accordance with the size of the artery of interest. This is because the varying image contrast during image acquisition creates artifacts. If the arteries have a high concentration of contrast for only a short period of time when the center of k-space is acquired, then the artifacts will be larger, making it possible to evaluate only the largest of arteries. In order to see small arteries free of artifacts, it is necessary to have a high concentration of gadolinium in the artery for a substantial fraction of the image acquisition time, including the period corresponding to acquisition of the center of k-space. In this regard, the duration for which the magnetic resonance contrast agent is administered at a maximum or elevated rate during collection of image data corresponding to the center of k-space may be adapted according to the size of the artery of interest. This provides for a period of overlap between a maximum or elevated concentration of contrast in the artery of interest and mapping of the center of k-space (i.e., overlap correlation factor). The overlap correlation factor may be defined as the amount of time during which an elevated or maximum arterial contrast exists in the artery of interest relative to the collection of image data representing the center of k-space. The overlap correlation factor may also be defined as the duration of overlap between the collection of image data representative of the center of k-space and a maximum or elevated rate of injection of the contrast agent. Where the artery of interest is relatively large (e.g., the aorta), an elevated or maximum injection rate of the contrast agent may overlap with the collection of image data representative of the center of k-space for a shorter period of time. In contrast, where the artery is relatively small (e.g., a renal artery), the contrast agent may be administered at an elevated or maximum rate for a longer period of time during the mapping of the center of k-space.

Further, when imaging larger arteries during the magnetic resonance angiography sequence, in a preferred embodiment, an elevated or maximum concentration of contrast agent in the artery of interest is provided for at least 20% of the time during which image data corresponding to the center of k-space is collected; and preferably, an elevated or maximum concentration of contrast in the artery of interest is maintained for between 20% to 50% of the mapping of the center of k-space. This, translates into correlating a period of substantially elevated or maximum rate of injection with the period of collection of image data corresponding to the center of k-space so that during at least 20% of the time of mapping k-space, a substantially elevated or maximum concentration of contrast agent is maintained in the artery of interest relative to adjacent veins; and preferably about 50%.

When imaging smaller arteries, in a preferred embodiment, an elevated or maximum concentration of contrast agent in the artery of interest is provided for greater than 50% of the time during which image data corresponding to the center of k-space is collected; and in a more preferred embodiment, an elevated or maximum concentration of contrast in the artery of interest is maintained for greater than 75% of the mapping of the center of k-space. As a result, where the artery of interest is relatively small, the administration of the contrast agent may include a maximum or elevated rate of injection of the contrast agent of greater than 50% of the time of mapping of the center of k-space; and preferably between 50% to 85%, and most preferably greater than 75%. Under this circumstance, fewer artifacts are observed in the smaller vessels or arteries when the contrast is administered at a maximum or elevated rate over a longer period of the k-space mapping.

It is noted that, in the aforementioned embodiment, the period of a maximum or substantially elevated rate of injection may also be compensated according to other factors including, the time delay due to the delivery system, the location of the artery, and the physical condition of the patient.

During the acquisition of magnetic resonance angiographic image data corresponding to the center of k-space, it may be is important to avoid excessively rapid changes in arterial contrast concentration. Rapidly changing blood signal during acquisition of the center of k-space may create image reconstruction artifacts. These artifacts may be minimized when the arterial signal intensity is uniform. Further, these artifacts may be minimized by slowly changing the arterial concentration during acquisition of image data and especially during acquisition of the center of k-space.

In those instances where the invention is implemented using paramagnetic contrast agents, infusion is at a rate that will provide a concentration of the agent in the arteries, such that the arteries will have at least 50% more signal than any background structures, including veins, in the final image. In a preferred embodiment, the concentration of contrast agent will cause the longitudinal relaxation time (T1) of the protons in the arteries to be shorter than protons in any of the background material. Where the contrast agent causes the arteries to appear black in the final image (e.g., where the contrast agent shortens T2*, for example, some Fe powders), the contrast agent should be infused at a rate and amount to insure that the effective transverse relaxation time (T2*) in the arteries is shorter than in any of the background material.

Any apparatus suitable for magnetic resonance imaging (MRI) of a portion of an animal body, for example, a human, may be used for acquisition of image data in the method of this invention. In particular, apparatus and imaging methods for magnetic resonance angiography are known in the art (see, e.g., U.S. Pat. Nos. 4,718,424; 5,034,694; and 5,167,232, incorporated herein by reference), and these may be used with the method of MRA with dynamic intravenous injection of magnetic resonance contrast agents taught herein, subject only to the constraints taught below.

The parameters of the imaging method of the magnetic resonance angiography sequences are discussed immediately below with respect to gadolinium chelates. It should be noted that other magnetic resonance contrast agents may be employed in practicing the present invention including paramagnetic contrast agents, such as those described by Marchal, et al., in Potchen, et al., eds., supra, pp. 305–322, the text of which is incorporated herein by reference.

Injection Parameters

Gadolinium chelates are paramagnetic agents which shorten the longitudinal relaxation time, T1, of blood according to EQUATION 1:

$$\frac{1}{T1} = \frac{1}{1200} + Relaxivity \times [Gd] \qquad (1)$$

where:
(1) the longitudinal relaxation time (T1) of blood without gadolinium is 1200 milliseconds; and
(2) [Gd] is the blood concentration of a gadolinium chelate.

With reference to EQUATION 1, to achieve an arterial blood (T1) that is short compared to adjacent fat (T1=270), it is necessary to substantially elevate the arterial blood concentration of the contrast agent in the artery of interest to be greater than ($\frac{1}{270}$ milliseconds–$\frac{1}{1200}$ milliseconds)/relaxivity of the contrast agent (or 2.9/seconds*relaxivity). Thus, the artery of interest includes a substantially elevated concentration of the contrast agent when that concentration is greater than 2.9 seconds$^{-1}$ relaxivity$^{-1}$ of the contrast agent.

A substantially elevated rate of infusion provides a substantially elevated concentration of the contrast agent in the artery of interest. That is, a substantially elevated rate of infusion provides an arterial blood concentration of the contrast in the artery of interest which is greater than 2.9 seconds$^{-1}$ relaxivity$^{-1}$ of the contrast.

As reflected in EQUATION 2, below, the arterial blood [Gd] may be expressed in terms of the intravenous injection rate and the cardiac output during dynamic imaging at times short as compared to the recirculation time.

$$[Gd]_{arterial} = \frac{Injection\ Rate}{Cardiac\ Output} + [Gd]_{venous} \qquad (2)$$

As long as the gadolinium chelate is sufficiently small, the gadolinium chelate will rapidly redistribute into the extracellular compartment as it passes through the capillary bed and the venous concentration will be low or negligible compared to the arterial concentration. The relationship between the longitudinal relaxation time of arterial blood and the injection rate may then be determined by combining EQUATION 1 and EQUATION 2, as stated below in EQUATION 3:

$$Injection\ Rate = \frac{\left[\frac{1}{T1} - \frac{1}{1200}\right]}{Relaxivity} \times Cardiac\ Output \qquad (3)$$

To achieve contrast between arterial blood and background tissue, the longitudinal relaxation time of the arterial blood should be reduced to less than that of the background tissues. Of all types of background tissues, fat (T1=270 msec) typically has the shortest longitudinal relaxation time. Assuming a typical minimum resting cardiac output of 0.0005 Liters/Kg-sec and requiring the longitudinal relaxation time to be less than 270 milliseconds simplifies EQUATION 3 to EQUATION 4 as shown below:

$$Injection\ Rate > \frac{0.0015\ L/Kg - sec^2}{Relaxivity} \qquad (4)$$

By way of example, gadopentetate dimeglumine, gadodiamide, and gadoteridol are three paramagnetic gadolinium chelates that are is readily available and rapidly redistribute into the extracellular fluid compartment. The relaxivities of gadopentetate dimeglumine and gadoteridol are 0.0045/molar-second. Based upon the aforementioned and using EQUATION 4, the minimum injection rate is greater than 0.033 millimole/Kg-minute.

With continued reference to EQUATION 4, a rate of infusion which is greater than 0.0015 Liters/Kg-sec$^2$ divided by the relaxivity may provide a maximum concentration of the contrast agent in the artery of interest. That is, infusing the contrast into the patient at a rate of greater than 0.0015 Liters/Kg-sec$^2$ divided by the relaxivity may yield a maximum arterial blood concentration of the paramagnetic contrast agent.

The total dose of gadolinium chelate required may be determined by multiplying the injection rate by the imaging time. For a relaxivity of 4.5/millimolar-second, and an imaging time of 5 minutes (300 seconds), the dose should substantially exceed 0.1 millimole/kilogram.

The dose of the gadolinium chelate may be within the range of 0.05 millimoles/kilogram body weight to 1 millimoles/kilogram body weight depending upon the time required to obtain the image. It should be noted that the dose of the contrast should not be too high such that there may be undesirable toxicity or T2 effects. In a preferred embodiment, the dose of the gadolinium chelate is within the range of 0.2 millimoles/kilogram body weight to 0.4 millimoles/kilogram body weight. In a more preferred embodiment, the dose of the gadolinium chelate is about 0.3 millimoles/kilogram body weight.

In those instances where the contrast injection times are longer than the recirculation time, the longitudinal relaxation time of arterial blood tends to be even shorter since a fraction of the gadolinium chelate will recirculate. It should be noted that a T1 of 270 ms (corresponding to the brightest background tissue fat) is equivalent to a gadopentetate dimeglumine concentration of 0.6 millimole/liter.

FIG. 1 illustrates the longitudinal relaxation time (T1) of blood as a function of infusion time and the total paramagnetic contrast dose for a paramagnetic contrast compound having a relaxivity of 4.5/millimolar-second. An examination of FIG. 1 reveals that the shortest T1 occurs with the shortest infusion time and the largest gadolinium dose. For typical imaging times of 3 to 5 minutes, FIG. 1 further reveals that the dose should be of the order of 0.2 millimoles/ kilogram or larger in order to achieve a longitudinal relaxation time of blood significantly shorter than that of the brightest background tissue fat (T1=270) for the entire duration of imaging.

It should be noted that higher doses of gadolinium and gadolinium chelates with higher relaxivity may also improve image quality.

Imaging Parameters

Any suitable T1 weighted magnetic resonance imaging sequence may be used during injection of the paramagnetic contrast. Suitable imaging sequences will be readily apparent to the skilled practitioner and are described in Potchen, et al., eds., supra. The following criteria for selection of preferred imaging parameters are based on experience in over 100 patients on a 1.5 Tesla General Electric signa magnet with version 4.7 software. A three-dimensional Fourier Transform (volume) acquisition (3D FT) is preferred in the abdomen because of its intrinsically high spatial resolution and high signal-to-noise ratio, even with a large, body coil. The gradient echo (gradient recalled) pulse sequences are preferred since they allow a short TR (repetition time) which allows a shorter imaging acquisition time. Short imaging times have the advantage of allowing the same total gadolinium dose to be injected at a faster rate.

Spoiled Versus Non-spoiled Gradient Echo Imaging

It should be noted that one might expect steady state gradient echo imaging (GRASS) to be preferable to the spoiled gradient echo imaging because the long T2 (transverse relaxation time) of blood increases the steady state blood signal. However, this effect enhances veins more than arteries, because the fast, pulsatile flow of arterial blood spoils its steady state component. In theory, this may have the paradoxical effect of reduced arterial contrast. In practice, there may only be a small difference between the spoiled and unspoiled techniques. In patients with slow arterial flow (which is not self-spoiling), steady state gradient echo may be preferred. A spoiled gradient echo pulse sequence (SPGR) was chosen for most of the studies described herein to simplify the theory and analysis to reduce the potential for differential steady state magnetization between arterial blood, slower venous blood and background tissue.

Echo Time

Because the brightest background tissue is fat, it is preferable to use a TE (echo time) where fat and water are out of is phase, thereby achieving an incremental improvement in vessel-to-background contrast. At 1.5 Tesla, this occurs about every 4.6 msec beginning at 2.3 msec which corresponds to a TE of 2.3, 6.9, 11.5, . . . msec. The shortest of these possible TE values (6.9 msec in the studies described herein) is preferred. Shorter TE's tend to minimize the effects of motion related phase dispersion.

Repetition Time

In a preferred embodiment, TR should be as short as is possible. A TR of 24–25 msec was the shortest possible on the equipment used for the studies described herein. As the TR is shortened, the flip angle must be adjusted to maintain the optimal T1 weighing.

Flip Angle

With a gadolinium chelate dose of 0.2 millimoles/ kilogram and a 3–5 minute injection time and imaging time, the longitudinal relaxation time of the arterial blood is predicted to be in the order of 150 to 200 milliseconds. It will, however, be shorter as a result of the recirculation time being less than 3–5 minutes. The relative signal intensity, SI, in a 3D FT spoiled gradient echo acquisition as a function of blood T1, TR, T2, T2*, flip angle σ, and proton density N(H) may be expressed as stated in EQUATION 5, below, and calculated accordingly.

$$SI = N(H) \frac{1 - \exp\left(-\frac{TR}{T1}\right)}{2 - \cos(\alpha)\exp\left(-\frac{TR}{T1}\right)} \sin(\alpha)\exp\left(-\frac{TE}{T2^*}\right) \quad (5)$$

Figure 2:
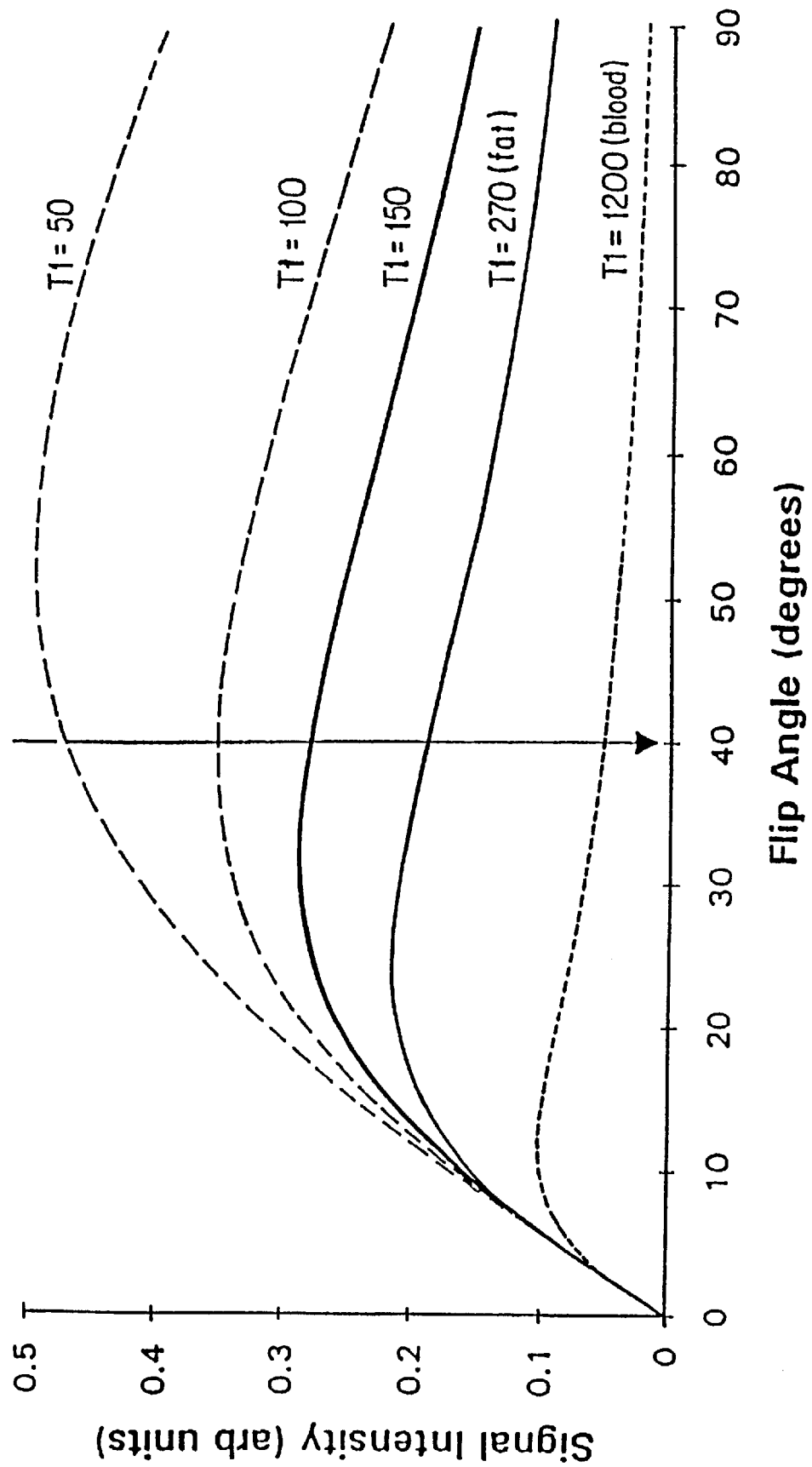
FIG. 2 illustrates calculated magnetic resonance signal intensity as a function of flip angle for 5 different longitudinal relaxation times (T1) assuming a spoiled, 3D volume acquisition with TR equal to 25 msec and TE<<T2*.

FIG. 2 graphically illustrates relative signal intensity for T1 equal to 50, 100, 150, 270 (fat), and 1200 (blood) under the following conditions: (1) TR=25 milliseconds, and assuming TE is small compared to T2* (the observed transverse relaxation time). FIG. 2 reveals that a flip angle of about 40 degrees is optimal for maximizing blood-to-background tissue (fat) contrast when the longitudinal relaxation time (T1) of blood is of the order of 200 milliseconds. For larger gadolinium doses with faster injection rates, a larger flip angle may be more appropriate.

Volume Orientation

In order to minimize the image acquisition time, the imaging volume should be made as thin as possible while containing the arteries of interest. In this regard, it may be useful to orient the image volume for maximum in-plane coverage of the vessels of interest as opposed to the perpendicular orientation required for optimal time-of-flight magnetic resonance angiography. Optimizing the orientation and minimizing the thickness of the imaging volume is facilitated by first acquiring a conventional black-blood or time-of-flight MRI to use as a guide for precise localization. Phase and frequency encoding axes should be oriented such that cardiac and respiratory motion artifacts do not superimpose on the vessels of interest. Generally, for imaging the aorta-iliac system, the imaging volume should be oriented coronally, and the phase encoding axis should be set right-to-left. For imaging the thoracic aorta, a sagittal orientation is preferred and for imaging the subclavian arteries, an axial orientation is preferred.

Partitions

The number of partitions (slices) is determined by the thickness of the image volume divided by the partition thickness. The partition thickness is the image resolution along the axis perpendicular to the plane of the partitions. It may be useful to employ thin partitions in order to have high image resolution. The image acquisition time, however, linearly increases with the number of partitions. As a result, keeping the image acquisition time short requires minimizing the number of partitions.

It should be noted that there may be a loss of signal-to-noise as the voxel size is decreased by using higher resolution pixels. Generally, 0.5 to 2 millimeter resolution with 28 to 60 partitions is adequate for the aorta and major branch vessels. The skilled practitioner will balance the need to increase resolution by decreasing voxel size with the need to avoid excessive periods of time to acquire image data.

Field-of-View

The field-of-view must be made large enough to avoid excessive wrap-around artifact. Wrap around artifacts occur when there are structures outside the field of view along the phase encoding axis. These structures are mapped by the phase encoding process to superimpose on structures within the field of view.

In addition, because of the limited number of pixels along the frequency encoding axis and time penalty for each additional pixel along the phase encoding axis, it is also desirable to make the field-of-view as small as possible in order to maximize image resolution with the minimum image acquisition time. Generally, for imaging the abdominal or thoracic aorta, a field-of-view of about 36 centimeters is appropriate for most patients. It may be increased for larger patients and reduced for smaller patients. Smaller field-of-views may be used for other parts of the body.

Use of a no-phase wrap algorithm is a less preferred embodiment. Under the circumstance of this invention, this has a disadvantage of generally requiring more imaging time and, as a result, a larger gadolinium dose.

Coils

It is preferable to use the smallest possible coil in order to minimize noise. There is also an advantage to coils that encircle the body part of interest such that the signal will be homogeneous throughout the entire field-of-view.

Patient Positioning

The patient should be positioned such that the body part being imaged remains stationary during the acquisition of image.

Cardiac and Respiratory Motion Compensation

The phase artifact related to respiratory and cardiac motion may be minimized by combining the T1 weighted imaging sequence with respiratory or electrocardiographic gating. Gating has the disadvantage of increasing the scan time—particularly in patients with irregular rhythms. Compensation techniques in which the acquisition of the image data in k-space is matched to the respiratory and or cardiac cycle may eliminate some phase artifact without significantly increasing the scan time.

In imaging regions of the body that move substantially with respiration (e.g., the renal arteries) it may be useful to acquire data while the patient is holding his breath. This may require shortening the duration of the image acquisition time to under one minute. If the patient cannot hold his breath for the entire period of image acquisition, than it may be useful to hold the breath during acquisition of image data corresponding to the center of k-space and breathing only during acquisition of data corresponding to the periphery of k-space.

Pre-scanning

The pre-scanning process is used to tune to the optimum frequency and to optimize the receiver gain. In the pre-scanning process, it is necessary to compensate for the changes in the patient's magnetic resonance signal that will occur during the contrast injection. In those instances when the paramagnetic contrast agent is a gadolinium chelate, it is preferable to tune to the water peak. About a 20% to 50% margin should be incorporated into the receiver gain setting to allow for increased signal during contrast administration.

Premedication

Premedicating patients with an analgesic or sedative such as diazepam may be useful for at least two reasons. Firstly, it may help the patient to tolerate the claustrophobic sensation of being within the magnet thereby reducing voluntary motion artifacts. Secondly, and more importantly, its relaxation and cardiac depressant effects tend to reduce the cardiac output. A lower cardiac output results in a higher arterial contrast concentration which thereby improves the image quality. This result is opposite from conventional magnetic resonance angiography which is degraded when the cardiac output decreases. By reducing the cardiac and respiratory rates, analgesics and sedatives may minimize the fraction of the image acquisition that is adversely affected by cardiac and respiratory motion artifacts.

Magnetic Resonance Contrast Agents

As mentioned above, many different magnetic resonance contrast agents may be employed when implementing the present invention; for example, numerous paramagnetic contrast agents are suitable. As mentioned above, gadolinium compounds, for example, paramagnetic gadolinium chelates, such as gadopentetate dimeglumine, gadodiamide, and gadoteridol, are readily available and rapidly redistribute into the extracellular fluid compartment. Other gadolinium compounds are acceptable. In general, preferred is contrast agents have a high relaxivity, rapid redistribution into the extracellular fluid compartment, and are readily extracted from the capillary bed. It should be noted that, contrast agents that are extracted or degrade in the capillary bed are preferred in the present invention.

In particular, gadolinium chelates are commercially available from such companies as Bristol Meyers (under the name "ProHance"), Berlex (under the name "Magnevist"), and Nycomed USA (under the name "OmniScan"). It should be noted that the gadolinium chelate which is commercially available from Nycomed appears to facilitate greater contrast enhancement between the artery and the surrounding veins and tissue.

Injection

In a preferred embodiment, the type or form of injection of the paramagnetic contrast is intravenous. The injection of the paramagnetic contrast is performed intravenously in order to eliminate or reduce the complications associated with the catheterization required for arterial injections.

The specific site of injection is important for several reasons. The site of injection should be remote from the "region of interest"; that is, the region that is to be scanned. For example, when imaging the abdominal aorta, intravenous injection of the paramagnetic contrast into an arm vein is preferred. Use of a leg vein should be avoided. Further, there may be some benefit in avoiding the antecubital fossa because the patient may bend the elbow during a long (3–5 minute) period of injection which may result in extravasation of the contrast into the subcutaneous tissues. As a result, under this condition, a forearm or upper arm vein may be preferable.

In those instances where an artery in the arm is to be imaged, the site of the injection may be a leg vein or a vein in the opposite arm. Here, the site of injection is remote from the "region of interest", i.e., the artery in the arm.

Moreover, it is important to adapt the timing of a maximum or elevated rate of infusion of the contrast agent to correlate with the collection of image data which corresponds to the center of k-space. As will be discussed in more detail below, correlating the infusion rate with the mapping of k-space insures that the image data representative of the center of k-space is collected over some period during which a maximum or elevated concentration of contrast agent is maintained in the artery of interest relative to adjacent veins. There are several manners of adapting the timing of a maximum or substantially elevated rate of infusion to correlate a maximum or substantially elevated concentration of contrast agent with the mapping of k-space, including adjusting the timing to account for the time delay in the delivery or infusion apparatus, the size and location of the artery of interest, the type of pulse sequence employed by the imaging apparatus, and the condition of the patient.

Figure 3:
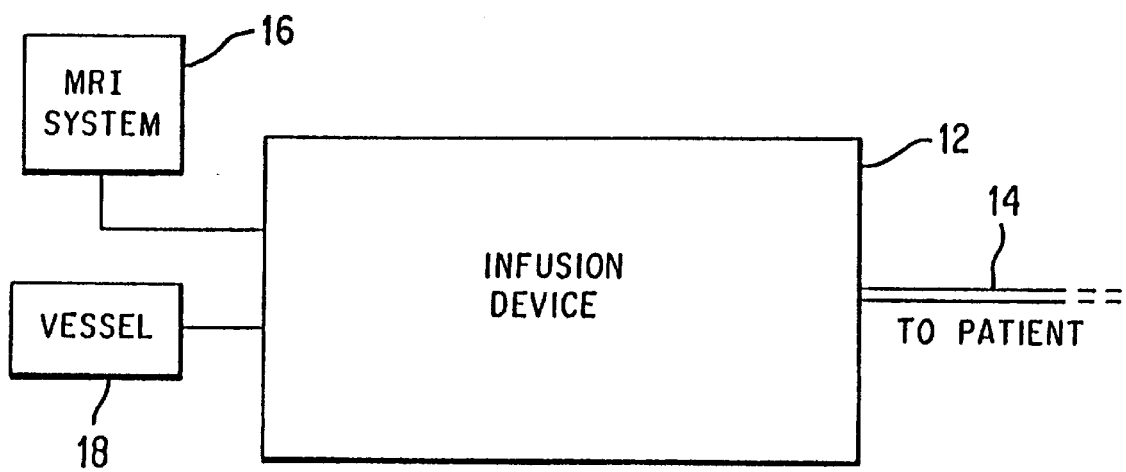
FIGS. 3, 4, 5A and 5B, and 6A–C are block diagram representations of mechanical infusion devices and configurations, according to the present invention.
Figure 4:
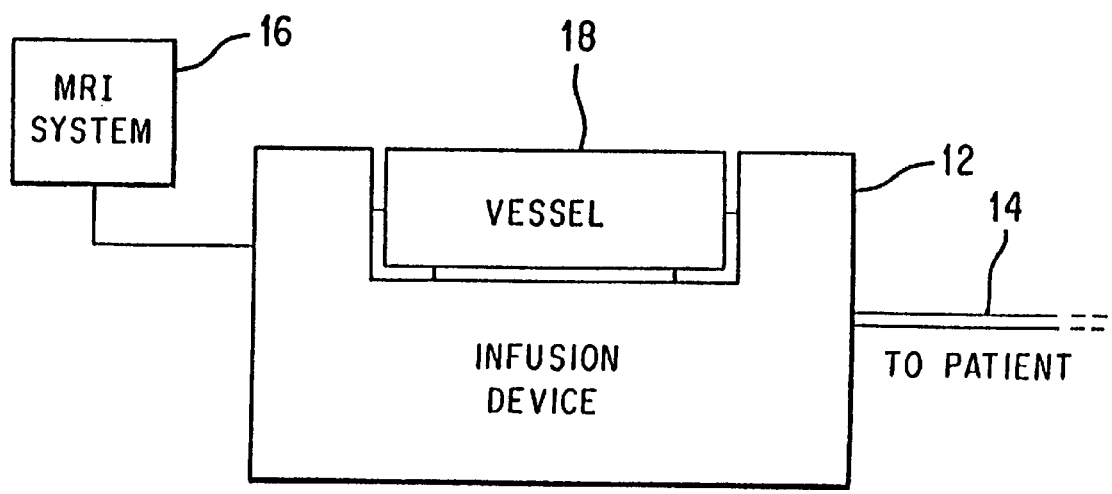

In a preferred embodiment, as illustrated in FIGS. 3 and 4, a mechanical infusion or injection device 12 is an automated type of injector having reliable and consistent operating conditions. The infusion device 12 is employed to inject the magnetic resonance contrast agent into the vein of the patient at an infusion rate sufficient to provide contrast enhancement of an image of an artery relative to veins in the field of view of the magnetic resonance image and substantially throughout the period of acquisition of image data. The infusion device 12 couples to the patient using conventional techniques, for example, appropriately selected tubing 14 which permits fluid flow between the mechanical infusion device 12 and the patient. Such tubing may be, for example, an angiocatheter.

A mechanical injector is preferred because of the greater reliability and consistency when compared to injecting by hand. Since the magnetic field interferes with normal functioning of electronic devices, a pneumatic powered, spring loaded or other non-electric pump may be suitable. It should be noted, however, is that an electrical pump may be used if its operation is unaffected by the operation of the magnetic resonance imaging system, e.g., if the pump is adequately shielded or if it is located sufficiently far from the magnet.

In one preferred embodiment, the mechanical infusion device 12 is coupled to the magnetic resonance imaging system 16 to facilitate proper or desired timing between the injection of the magnetic resonance contrast agent and the acquisition of the image data, in addition to providing proper or desired rates of infusion of the contrast agent.

In another preferred embodiment, proper or desired timing and rates of infusion of the contrast agent are controlled through a control mechanism at the mechanical infusion device 12. That is, the mechanism that controls the infusion timing and rates of infusion is implemented within the mechanical infusion device 12. In this circumstance, the mechanical infusion device 12 is a "self-contained" unit. For example, the infusion rate may be controlled with an adjustable fluid flow resistor.

As mentioned above, the infusion device 12 injects the magnetic resonance contrast in a controlled manner. The contrast may be contained in a vessel. As illustrated in FIGS. 3 and 4, the mechanical infusion device 12 is coupled to a vessel 18 which contains the magnetic resonance contrast agent. In one embodiment, the vessel 18 may contain a sufficient quantity of contrast agent for one application of the invention or one sequence of the plurality of the magnetic resonance angiography sequences, e.g., a single use vessel. In an alternative embodiment, the vessel 18 may contain a quantity which allows several applications of the invention, e.g., a reservoir type of vessel. As is illustrated in FIG. 3, the mechanical infusion device 12 may be adapted to receive the vessel 18 somewhat like a fountain pen receiving an ink cartridge. In an alternative embodiment, as illustrated in FIG. 4, the infusion device 12 may be coupled to the vessel 18 using conventional methods.

Figure 5A:
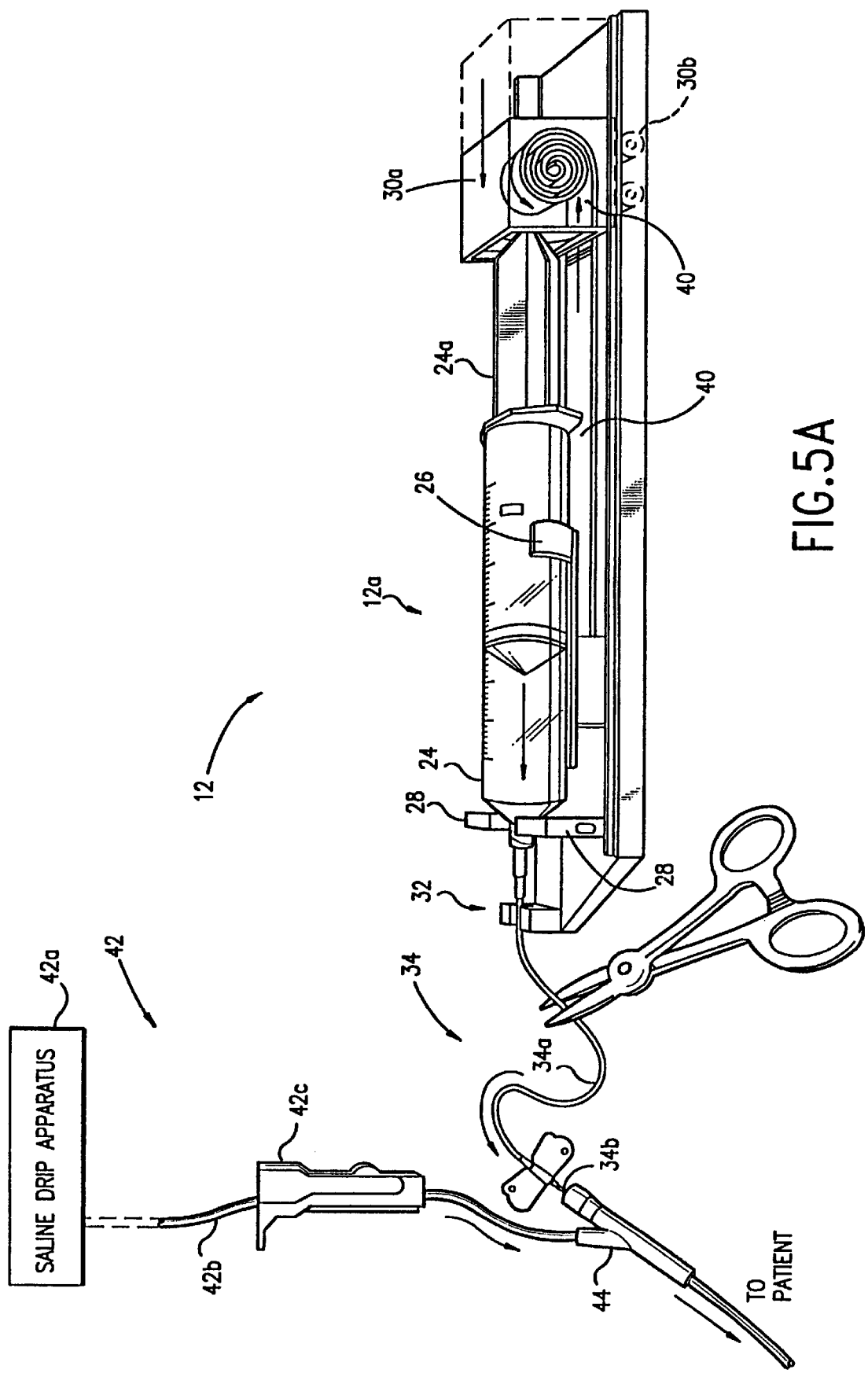
Figure 5B:
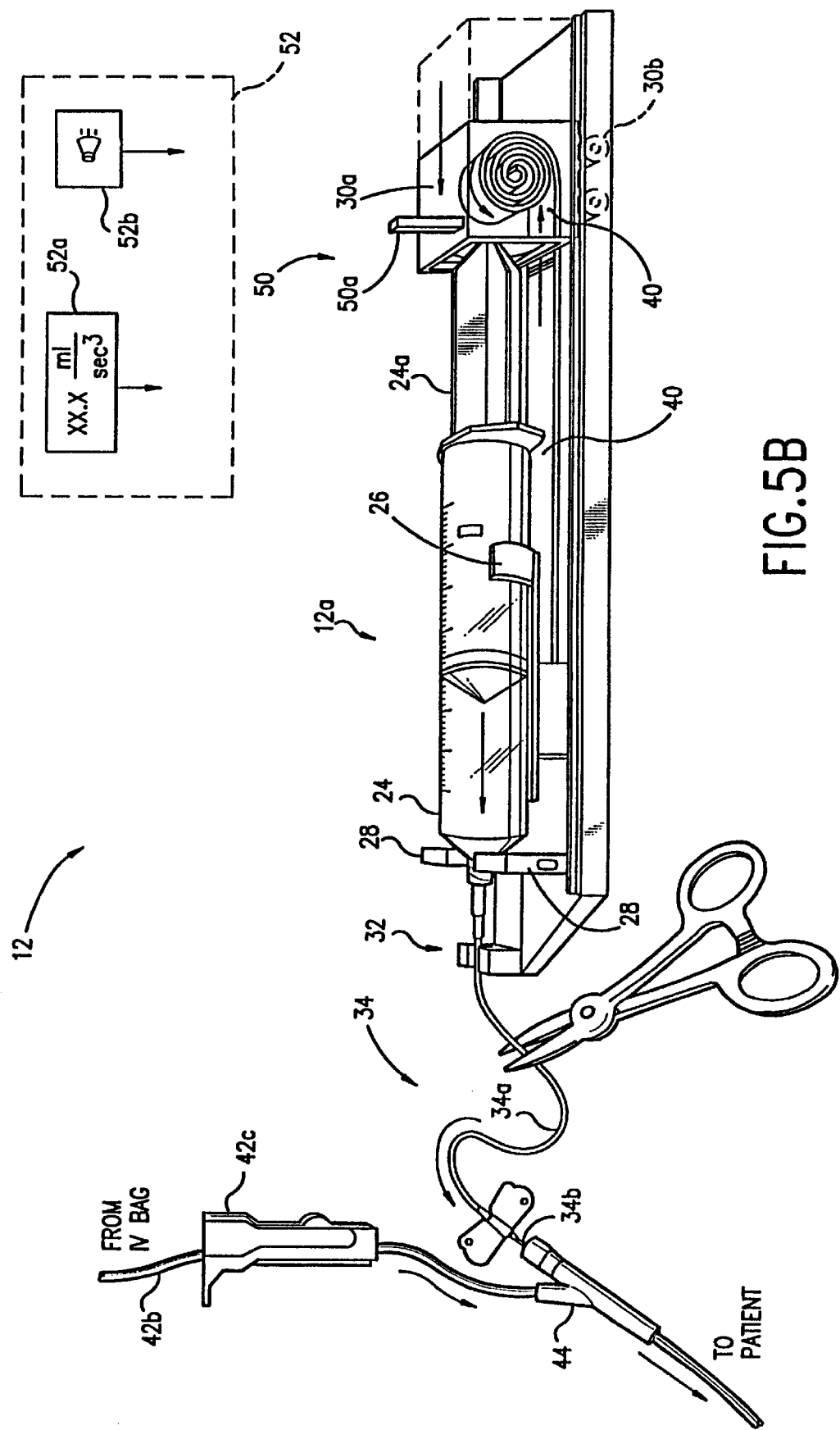

FIGS. 5A and 5B illustrate a mechanical infusion device 12 in more detail. The mechanical infusion device 12 of FIGS. 5A and 5B include several of the components described and illustrated in U.S. Pat. Nos. 4,202,333; 4,298,000; 4,430,079; and 4,597,754. The descriptions of these patents, including several of the components of the mechanical infusion device 12 described therein, are incorporated herein by reference. Moreover, such infusion devices are commercially available from 3M Corporation and their product specification sheets are also incorporated by reference.

In those instances where the mechanical infusion device 12 is employed within the environment of the magnetic field, the infusion device 12 should be fitted or manufactured with magnetic resonance compatible material. For example, the infusion devices which are commercially available from 3M Corp., should be fitted with a magnetic resonance compatible spring. This requires manufacturing the spring from non-magnetic materials, for example, plastic or certain metal alloys such as eljaloy or inconel.

To implement the techniques of the present invention and thereby obtain a constant or variable rate of infusion of the magnetic resonance contrast agent, the device 12 of FIGS. 5A and 5B may include a spring which has a constant width and thickness in order to exert a constant force; or, alternatively, the spring may have a variable width and/or variable thickness to provide a variable spring force. Under this circumstance, the infusion rate may be controlled to be either constant or variable by design of the spring and, in effect, pre-programmed by selection of the spring's design parameters.

In one embodiment, the infusion device 12 infuses the magnetic resonance contrast agent at a variable infusion rate having a maximum or elevated rate of infusion which temporally correlates with the acquisition of image data which is representative of the center of k-space. Under this circumstance, data representative of the center of k-space is acquired during the period of a maximum or substantially elevated arterial gadolinium concentration in the artery of interest.

As mentioned above, in one preferred embodiment, the timing of a maximum or substantially elevated rate of injection may be correlated to the mapping of the center of k-space in accordance with the particulars of the delivery systems (e.g., physical length of the catheter/tubing), the location of the artery of interest, the size of the artery of interest, and/or the physical condition of the patient. Such a correlation technique allows image data corresponding to the center of k-space to be collected during a period of maximum or substantially elevated contrast concentration in the artery of interest.

It should be noted that the center of k-space may be characterized as 10% to 75% of the total k-space data which corresponds to the lowest spatial frequency information.

It should be further noted that a substantially elevated concentration of the contrast agent in the arterial blood may be described as a concentration which is greater than 2.9 $seconds^{-1}$-$relaxivity^{-1}$. As mentioned above, a substantially elevated rate of infusion provides a substantially elevated concentration of the contrast agent in the artery of interest. In this regard, a substantially elevated rate of infusion provides a concentration of the contrast in the artery of interest which is greater than 2.9/seconds-relaxivity (of the contrast).

Further, as mentioned above, a rate of infusion of the contrast agent which is greater than 0.0015 Liters/Kg-$sec^2$ divided by the relaxivity may provide a maximum arterial blood concentration of the paramagnetic contrast agent in the artery of interest.

In one preferred embodiment, the infusion device 12 may be designed to accommodate a 50 cc syringe having a fluid capacity of 60 cc and containing one dose of the contrast agent. The infusion device 12 may also be designed to permit an external (manual) force on the syringe to modify or customize the rate of infusion of the contrast agent. This external force is separate from the force of the spring of the infusion device 12.

Further, the infusion device 12 may include a flow rate indicator 50 (FIG. 5B) to provide an indication of flow rate of the contrast agent to the patient. Under this circumstance, the operator may visually or audibly observe, in a rather simple manner, the rate of flow of the contrast agent. This will allow the operator to exert an external force more accurately (both in the amount of force applied and in a timing sense) thereby facilitating a modification of the predetermined injection rate. Further, in an automated-type of infusion device, the flow rate indicator 50 permits the operator to visually or audibly monitor a "pre-programmed" infusion rate or sequence.

Briefly, reference to FIG. 5A, the mechanical infusion device 12 further includes syringe 24, a syringe clamp 26, a syringe restraint or stop 28, a block and spring housing 30a, roller bearings 30b, a reflux valve 32 and a catheter 34 having tubing 34a and a needle 34b (butterfly type). The syringe 24 contains the contrast agent to be administered to the patient during magnetic resonance imaging. A plunger 24a of the syringe 24 is engaged by a spring 40 which is housed in the block and spring housing 30a. In operation, the spring 40 engages the plunger 24a to pressurize the syringe 24. The syringe is maintained in a stationary position within the mechanical infusion device 12, and in particular, in housing base 12a, via the syringe clamp 26 and the syringe restraint 28.

In one preferred embodiment, the mechanical infusion device 12 is coupled to a saline drip apparatus 42 (saline drip 42a, tubing 42b and roller clamp 42c). The saline drip apparatus 42 is applied to an input of a y-port connector 44. The syringe 24 is applied to the other input of the y-port connector 44. This conventional configuration facilitates a saline flush following the administration of the contrast agent within the syringe 24. In those instances where the tubing leading from the saline drip apparatus 42 to the y-port connector 44 has a one-way valve to prevent reflux of contrast, it is acceptable to leave the saline drip "on" during infusion. Under this circumstance, as soon as the infusion of the contrast agent is complete, the drip infusion will automatically resume to "flush" gadolinium within the intravenous tubing and deliver the contrast agent which remains in the tubing to the patient.

The rate of injection of the contrast agent from the syringe 24 is determined or controlled, in large part, by the size or gauge of the needle 34b, which functions as a fluid flow restrictor according to Poiseulle's Law. The rate of injection is also controlled by the amount of force that the spring 40 (the restoring force of the spring 40) applies to the plunger 24a of syringe 24, the syringe cross-sectional area, the gadolinium viscosity as follows:

$$\text{Infusion Rate} = \frac{\pi r^4 F}{8 L \mu A}$$

where:
r=radius of flow restricting needle lumen;
F=spring force;
L=length of flow restricting needle;
μ=viscosity of the fluid; and
A=cross-sectional area of the syringe.

Examining the infusion rate equation immediately above reveals that a variation of the syringe size (A), needle length (L), and/or fluid viscosity (μ) impacts the rate of infusion of the contrast agent. The viscosity of the fluid, however, may be dependent on the temperature of the contrast agent (gadolinium chelate). Thus, in those instances where the temperature of the contrast agent alters the viscosity of the contrast, the rate of infusion is also dependent on this "variable."

It should be noted, however, that the influence of viscosity on the flow rate may be substantially reduced by employing a fluid flow restrictor which minimizes the effects of viscosity on the rate of fluid flow.

In a preferred embodiment, the characteristics of the spring 40 (e.g., spring force) may be selected or designed such that the spring 40 applies a constant force upon plunger 24a throughout the period of contrast infusion. In another preferred embodiment, the characteristics of the spring 40 may be selected or designed such that the spring 40 applies a variable force on the plunger 24a. That variable force may correlate with the imaging process so that a maximum or substantially elevated injection rate provides a maximum or substantially elevated concentration of contrast in the artery of interest during the collection of image data which corresponds to the center of k-space.

The rate of injection, however, may be increased or decreased using a manual, spring loaded, or pneumatic injection rate adjustment mechanism which may be connected to various components of the device 12, including, the spring 40, the block and spring housing 30a, the roller bearings 30b, the plunger 24a, the tubing 34a, and/or the fluid flow restrictor 34b. FIG. 5B illustrates a manual injection rate mechanism 50 for allowing the operator to readily alter the rate of injection and thereby modify the rate of injection of the contrast agent to accommodate or implement a desired timing of an elevated or maximum rate of flow of the contrast agent.

The spring force should be sufficient such that the flow restrictor, required to give the desired flow rate, has a flow resistance that is much greater than any flow resistance in the intravenous line. The spring force should not be so high that a person of ordinary strength can not reduce or increase this force when a manual spring adjustment mechanism 50 is designed as the means for adjusting the rate of flow (i.e., the amount of external force applied to the spring) of the contrast agent. In general, a spring with about 5–10 pounds of spring force is suitable for 2–3 minute infusions and a higher spring force may be required for faster infusions. Infusions as short as 30 seconds may require a spring force of 20–30 pounds.

A fluid flow restrictor may be manufactured from, include or be comprised of a needle, a short piece of tubing of narrow calibre (e.g., an intravenous angiocatheter of 20 gauge or larger may be satisfactory), an orifice (for example made of ruby or sapphire), a focal compression of the IV tubing, or other mechanism which impedes the flow of fluid.

It should be noted that a precision orifice may offer several advantages when employed as a fluid flow restrictor. For example, in those instances where an incompressible fluid is to be administered, such as gadopentetate dimeglumine, gadoteridol, or gadodiamide, flow through an orifice is governed by the Bernoulli effect. In this regard, the flow rate of the fluid through the orifice is proportional to the square root of the pressure drop:

$$\text{Infusion Rate} = K = \sqrt{\left(\frac{F}{A}\right)}$$

where:
K=a constant determined by the geometry of the orifice;
F=spring force; and
A=syringe cross-sectional area.

Further, it should be noted that the pressure drop across an orifice is governed by inertial effects of the fluid; the viscosity of the fluid has little to no impact. As a result, an orifice minimizes the influence of the viscosity of the fluid on the rate of flow of the fluid. Under this circumstance, by using an orifice as a fluid flow restrictor, the Bernoulli effect predicts the same flow rate regardless of temperature of the fluid and regardless of which gadolinium compound is employed. Although in practice it is essentially impossible to entirely eliminate viscosity effects of the fluid, those effect are markedly reduced.

TABLE 1 provides the infusion rate, with respect to three MR contrast agents, for a variety of needles and flow restricting orifices when employed in an infusion device 12 substantially as illustrated in FIG. 5A where the spring 40 is a 6 pound-force spring and the syringe 24 is a 1 inch diameter, 50 cc syringe.

In those instances where the rate of flow of the fluid is dependent on the ambient temperature or the temperature of the contrast agent, consistent operation of the infusion device 12 may require either a temperature controlled operating environment or use of a fluid flow restrictor whose operational characteristics are essentially unaffected by the viscosity of the fluid (e.g., a precision orifice).

With reference to FIG. 5B, in a preferred embodiment, the rate adjustment mechanism 50 is a manual type including a lever 50a by which the user may increase or decrease the force applied to the plunger 24a. The lever 50a engages the plunger 24a and spring 40 so that the resulting force applied to the plunger 24a is essentially determined by the sum of the force applied to the plunger 24a (i.e., by the lever 50a) and the spring force, F. By employing this configuration, the user may increase or decrease the rate of injection at a particular moment of the imaging sequence. For example, increasing the infusion rate at about 10 to about 40 seconds prior to the acquisition of image data corresponding to the center of the k-space would cause an elevated or relatively high arterial gadolinium level to be maintained in the artery of interest during acquisition of image data corresponding to the center of k-space (typically it takes about 10–40 seconds for venous blood in the arm to circulate through the heart and lungs to reach the artery of interest). Such a technique may provide additional contrast enhancement of the image of the artery relative to veins and surrounding tissue.

The infusion device 12 of FIG. 5B further includes a flow rate indicator 52 to provide the operator an indication of a flow rate (injection rate) of the contrast agent to the patient. Here, the operator may visually or audibly observe the rate of flow of the contrast agent to thereby accurately control the rate of injection of the contrast agent into the patient; the operator may customize or modify the contrast injection rate.

The flow rate indicator may be implemented using an optical type sensor for sensing the linear motion of, for example, the plunger 24a, the spring 40, and/or the block and spring housing 30a, or the rotational motion of the roller bearings 30b. Such a mechanism permits an accurate measurement with little to no impact on the operation of the injection device 12, including the motion of the plunger 24a and the operation of the spring 40. That is, an optical type rate indicator has an advantage of not requiring physical contact with the contrast agent in the syringe 24 or spring 40.

It is noted, however, that a fluid flow or motion sensor may also be employed in the flow rate indicator 50. Such devices provide accurate information regarding the rate of flow of the contrast agent in the syringe 24 or in the tubing 34a.

As mentioned above, when the mechanical infusion device 12 is employed within the environment of the magnetic field, the materials used to fabricate the device 12 should be non-magnetic. That is, magnetic materials should be avoided when the device 12 is implemented in or near the magnetic field of the magnetic resonance imaging apparatus. In those instances, the spring 40 (FIGS. 5A and 5B) should be manufactured from non-magnetic materials, for example, eljaloy or inconel.

Figure 6A:
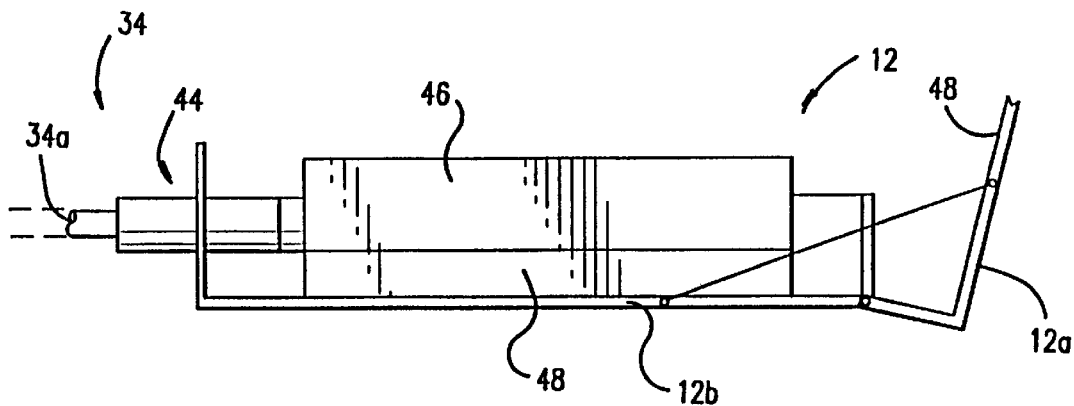
Figure 6B:
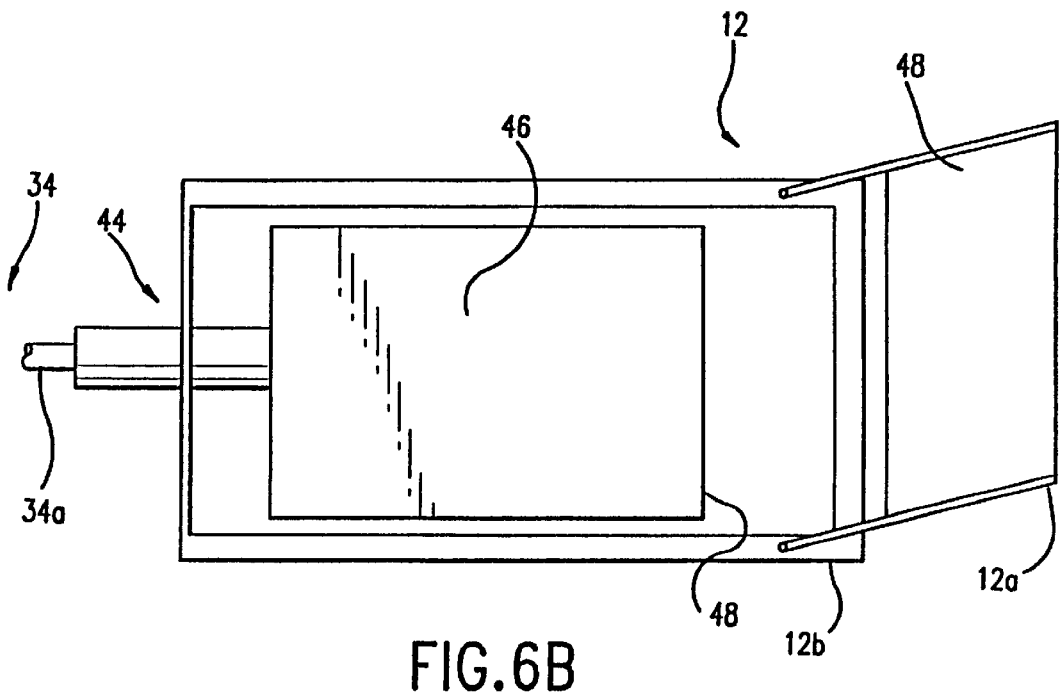
Figure 6C:
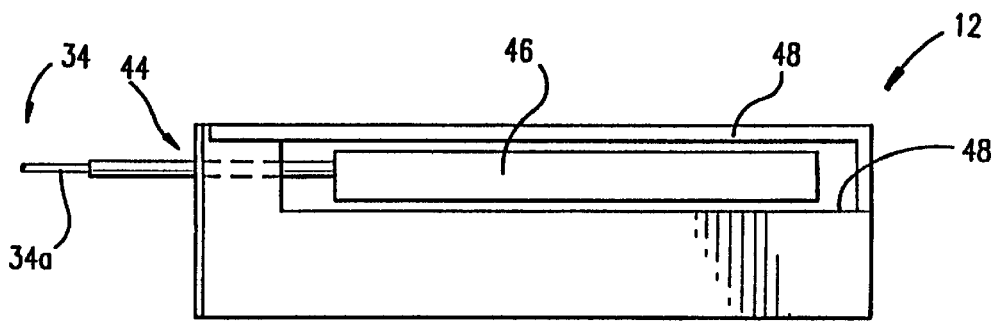

With reference to FIGS. 6A–C, the mechanical infusion device 12 may be implemented using a bag-cassette configuration. The bag 46 contains a contrast agent. Analogous to the syringe configuration of FIGS. 5A and 5B, the bag 46 may be placed into a cassette 48 which applies even pressure over the contact surface of the bag 46. In operation, the contrast agent then flows, similar to the syringe 24, from the bag, through the catheter 34 to the patient. As with the case with the syringe configuration, fluid flow control is provided by means of a fluid flow restrictor (i.e., the needle 34b) used in combination with a cassette 48 which provides the force.

It should be noted that the bag-cassette arrangement of FIGS. 6A–C may employ a saline drip apparatus 42 as well as a rate adjustment mechanism 50. As with the syringe configuration, the rate of injection may be increased or decreased using a manual, spring loaded, or pneumatic rate adjustment mechanism 50.

In some magnetic resonance suites, an opening exists in the wall dividing the magnet of the imaging apparatus and the control equipment (i.e., computer and other electronic devices). In these situations, standard infusion pumps (containing metal, magnetized material and electronic circuits) can be used from outside of the MR suite to implement the methods described herein.

In one preferred embodiment, a pump manufactured by Abbott, the Life Care 5000, may be implemented. The Life Care 5000 draws drugs (e.g., contrast agent) directly from a bottle and preloads it into a long length of tubing. The operating parameters of the Life Care 5000 may be preprogrammed to execute numerous infusion rates.

In another preferred embodiment, the injection rate for contrast is matched with the mapping of k-space so that a maximum or substantially elevated arterial gadolinium concentration correlates with acquisition of image data corresponding to the center of k-space. That is, the operating parameters of the pump may be pre-programmed to provide an injection rate for contrast agent which is matched with the mapping of k-space so that a maximum or substantially elevated rate of infusion occurs about 10–40 seconds prior to the collection of image data corresponding to the center of k-space.

This type of configuration offers several advantages including: (1) the contrast agent (gadolinium) need not be removed from its shipping containers into an intermediate container, for example, a syringe; (2) the programmability of the pump allows variable injection rates providing for a maximum rate at the peak when the center of k-space is being mapped (which may be the most It critical period during image acquisition); (3) operator control of the operating parameters.

It should be noted that the Life Care 5000 Pump may not be ideally suited for implementing all of the techniques described herein. For example, such deficiencies include the rates of injection of the pump, the degree of programmability of the flow delivery characteristics of the pump, and allowing the pump to administer contrast from multiple containers which will permit multiple 20 cc vials to be used.

As mentioned above, the precise timing of the injection of the paramagnetic contrast during performance the magnetic resonance angiography sequences provides preferential enhancement of an artery of interest relative to adjacent veins and background tissue. The injection of the paramagnetic contrast agent should temporally correlate to a period during which imaging data is being collected and preferably concurrent with the acquisition of image data. When implementing longer pulse sequences (greater than 2 minutes) or pulse sequences which collect image data representative of the center of k-space some time after initiation of image data collection, it is important that no contrast be administered prior to magnetic resonance scan since the contrast may leak into the background tissues and cause a degradation of the image. If some paramagnetic contrast or other magnetic resonance contrast has been administered prior to imaging, it is preferred to delay the arterial scan until this contrast has been excreted by the patient, in order to increase the probability of obtaining optimal images.

An exception to this requirement is when a small test dose of contrast or the like (sodium dehydrocholate, saccharin or is indocyanine green) is used to determine the circulation time prior to performing the dynamic injection with imaging. By infusing a small test dose of a few milliliters and then imaging rapidly the region of interest, it is possible to determine the time interval between contrast infusion and contrast arrival in the artery. This time may then be used to guide timing for the image acquisition in that it may facilitate more accurate correlation between the injection of the contrast agent and the acquisition of the data representative of the center of k-space. This time should roughly equal the time between the middle of the infusion and the moment of acquisition of the center of k-space for short infusions.

In those instances where the imaging apparatus employs pulse sequences having very short data acquisition periods the contrast agent may be injected before the initiation of collecting image data. Short pulse sequences may be characterized as those sequences for which the time required for contrast to circulate from injection site to the artery of interest becomes a significant fraction of the imaging time, for example, data acquisition periods of less than 2 minutes. Under this circumstance, injection of the contrast agent before acquisition of image data is necessary to allow circulation of the contrast agent in the patient and thereby correlate a maximum or substantially elevated arterial concentration with the collection of image data representing the center of k-space. Administering the contrast agent prior to the acquisition of image data would cause a relatively high arterial gadolinium level during the mapping of k-space. As discussed above, the relative timing between the administration of the contrast agent and the collection of image data representing the center of k-space should be adapted to account for the injection mechanism employed, the location of the artery of interest, the size of the artery of interest, and the physical condition of the patient. For example, the contrast may be administered about 10–40 seconds before collection of image data to account for venous blood in the arm to circulate through the heart and lungs to reach the artery of interest. Thus, the amount of time before acquisition of image data may depend on the configuration of the contrast delivery mechanism, the relative location of the artery of interest, the relative size of the artery of interest, and the condition of the patient, including the age of the patient. Employing these considerations in selecting and controlling the timing of the injection provide a more accurate alignment between the acquisition of data representative of the center of k-space and a period of maximum or substantially elevated contrast concentration in the artery of interest relative to adjacent veins.

In a preferred embodiment, a constant infusion should begin within a few seconds of initiation of the scan process. The contrast infusion should end about 20 or more seconds before the completion of the scan; this allows the intravenously injected contrast to circulate through the heart and into the arteries. A chaser of normal saline or other fluid may be used to insure injection of the entire dose of the paramagnetic contrast (e.g., gadolinium) and, in addition, to insure that there is sufficient venous return to propel the injected contrast to the heart. In a preferred embodiment, the contrast infusion rate is matched with the mapping of k-space so that the maximum arterial gadolinium concentration occurs during acquisition of the center of k-space. This may permit injecting over a shorter period of time to achieve either a higher injection rate or a lower contrast dose.

As discussed above, in order to adapt the timing of a maximum or substantially elevated rate of infusion and, in effect, a maximum or elevated arterial concentration of the contrast agent in the artery of interest, with the collection of image data corresponding to the center of k-space consideration should be given to the contrast agent delivery system or apparatus, the time interval for venous blood at the site of infusion to reach the artery of interest, the size of the artery of interest, and the location of the artery of interest. Each of these "variables" impact on the time between the maximum or elevated rate of injection and when a maximum or elevated arterial concentration in is the artery of interest is observed.

The inherent delay in the contrast delivery system depends on, for example, the length of the tubing 14, between the infusion device 12 and the patient. Such a delay, once measured or determined, may be considered a "constant" for a given delivery or infusion apparatus.

The time interval for venous blood at the site of infusion to reach the artery of interest (i.e., the "circulation time") depends on the location of the artery of interest and the physical condition of the patient. Typically, this time interval may vary from about 10 to about 40 seconds. The time interval may be longer if the artery of interest is far from the heart, for example, in the foot, or if the site of infusion is a peripheral vein such as in the hand.

Further, young, healthy patients with normal cardiac output tend to have a faster flow and a short circulation time, between 10–20 seconds (typically about 15 seconds). Older patients and patients with low cardiac output have a slower circulation times, between 20–40 seconds or more. The circulation time will also be longer for an IV in the hand compared to one in the upper arm. Central lines which inject directly into the SVC or right atrium will have the shortest circulation times.

In another preferred embodiment, the period of a maximum or substantially elevated rate of infusion of the magnetic resonance contrast agent to the patient is adapted according to the size of the artery of interest to correlate with the period of the collection of image data corresponding to the center of k-space. In this regard, where the artery of interest is relatively large (e.g., the aorta), a period of a substantially elevated or maximum injection rate may overlap for a smaller fraction of the period of collecting image data representative of the center of k-space than where the artery is relatively small (e.g., renal). For example, when imaging larger arteries, the administration of the contrast agent may include a period of a substantially elevated or maximum rate of contrast which provides a substantially elevated or maximum arterial concentration for less than 50% of the period during which the system collects image data corresponding to the center of k-space; and preferably between 20% to 50%. Where the artery of interest is relatively small, it is preferable that a period of maximum or substantially elevated rate of injection provide a maximum or substantially elevated concentration of the contrast in the artery of interest for more than 50% of the period of mapping the center of k-space; and preferably between 50% to 85%.

Figure 7:
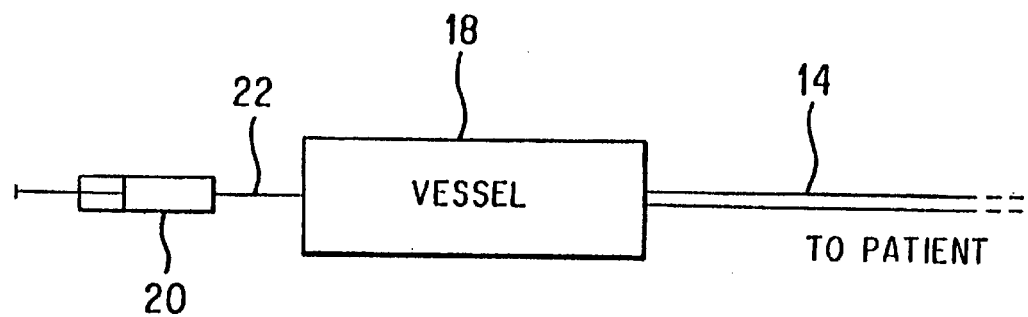
FIG. 7 is a block diagram representation of a manual injection configuration, according to the present invention.

With reference to FIG. 7, the infusion of the magnetic resonance contrast agent may be by way of manual means. In this embodiment, a syringe 20, having needle 22, is coupled to a vessel 14 containing the magnetic resonance contrast agent. The vessel 14 is coupled to the patient using conventional techniques, for example, appropriately selected tubing 14 which permits fluid flow between the vessel 18 and the patient, for example, an angiocatheter.

When injecting the contrast agent using a manual injector, i.e., injecting the magnetic resonance contrast agent by hand, during the magnetic resonance angiography sequences, in a preferred embodiment, the infusion "path" includes a fluid flow restrictor which adds resistance to the flow of gadolinium during administration into the body. It should be noted that a fluid flow restrictor may be, for example, a standard injection needle or small calibre angiocatheter. In FIG. 7, the fluid flow restrictor may be the needle 22 of syringe 20 and/or the angiocatheter 14. Use of small needles, short pieces of tubing of narrow calibre, an orifice, and/or small calibre angiocatheters may alleviate errors of injecting the contrast too rapidly and, as a result, depleting or running-out of contrast before completion of the scan or improperly correlating a maximum or elevated rate of infusion with the mapping of k-space. In a preferred embodiment, the needle size may be 22 gauge or smaller diameter (higher than or equal to 22 gauge) depending upon the viscosity of the contrast agent for an infusion of 2–4 minutes. Angiocatheter of 20 gauge may be suitable for infusions of about 30 seconds.

It may be convenient to preload the contrast into a vessel or length of tubing with luer lock or other appropriate connectors at each end of the tubing. It is then possible to use a single saline filled syringe to inject the contrast followed by a saline chaser without having to switch syringes or pumps. Saline is a preferred fluid to use as a chaser since it can be made isotonic with blood and is compatible with most intravenous fluids and pharmaceuticals that may already be flowing through a patient's IV line.

In a preferred embodiment, the contrast is infused slowly at the beginning and fastest in the middle of the acquisition. This type of injection pattern, based upon the fact that the contrast does somewhat contribute to venous and background tissue enhancement, avoids excessive contrast early in the acquisition.

Post-Processing

Post-processing of the scan data may be used. Maximum intensity projection (MIP) collapse images are useful for rapidly examining the entire arterial circulation within the region of interest. It may be useful to reformat and selectively collapse the data through the specific arteries of interest. Additional contrast may be obtained by digitally subtracting a pre-gadolinium acquisition from the dynamic gadolinium acquisition. Volume rendering may also be useful and is possible with these high is contrast volume data sets.

Immediately below are examples of results obtained from use of preferred embodiments of the present invention. The parameters of the examples are detailed therein.

Additional Sequences

After performing a dynamic contrast enhanced scan, it is possible to obtain additional MR angiogram images in which there is enhancement of both arteries and veins, as well as liver, spleen, kidney, and other organs. Phase contrast magnetic resonance angiography is also improved following the administration of magnetic resonance contrast. It may then be possible to combine a dynamically enhanced scan for visualization of primarily the arteries with one or more post-gadolinium (contrast agent) scans to resolve anatomic or physiological issues that may be important to a patient's condition.

EXAMPLE 1

Contrast between peripheral arteries and veins in images obtained by imaging dynamically during the administration of gadopentetate dimeglumine was investigated in sixteen patients referred for aorta-iliac magnetic resonance arteriography. These included 9 males and 7 females with a mean age of 72 ranging from 67 to 83. The indications for the study included hypertension (6), abdominal aortic aneurysm (AAA, 6) claudication (4) and renal failure (9). Some patients had more than one indication.

Parameters:

All imaging was performed on a 1.5 Tesla superconducting magnet (General Electric Medical Systems, Milwaukee, Wis.) using the body coil and version 4.7 software. A 3D FT, coronal, spoiled, gradient echo volume was acquired centered on the mid-abdomen. The imaging parameters included: 12 cm volume with 60 partitions, 2 mm partition thickness, TR of 25 msec, a TE of 6.9 msec, a flip angle of 40°, first order flow compensation, 36 centimeters field of view, 256 by 192 matrix. The imaging time was 5 minutes and 10 seconds. Frequency was set superior to inferior so that phase artifact from diaphragmatic and cardiac motion would not superimpose on the abdominal aorta and IVC. When possible, phase artifact noise was minimized by excluding the heart and lungs entirely from the field of view. No saturation pulses were employed. The volume data were reformatted through vessels of interest and also displayed as maximum intensity projections.

Gadopentetate Dimeglumine Injection:

After pre-scanning, venous access was obtained via a 22 gauge angiocatheter. A dynamic acquisition was then performed during hand injection of gadopentetate dimeglumine (Berlex Laboratories, Cedar Knoll, N.J.), 0.2 millimoles/kilogram. The injection was initiated within 5 seconds of initiating the image acquisition. The injection rate was constant (within the limitations of a hand injection) and timed to last until 10–20 seconds before completion of the scan. The injection included a 5 cc normal saline chaser to ensure injection of the entire gadopentetate dimeglumine dose. As a result, the gadopentetate dimeglumine ended approximately 30–40 seconds before completion of the scan and the saline chaser ended about 10–20 seconds before completion of the scan. In order to compare to the conventional, non-dynamic, gadolinium-enhanced MRA, a second, identical acquisition was then acquired without altering the imaging or prescan parameters.

Signal Measurements:

Signal intensity was measured in the abdominal aorta, IVC, iliac artery and vein, renal artery and vein, celiac trunk, SMA, portal vein, hepatic vein and background tissue (including fat, skeletal muscle, kidney, liver and spleen) for 7 regions of interest per measurement. As many of these measurements as possible were obtained from the central 20 partitions and all measurements were obtained from the central 40 partitions. Identical regions of interest were used to compare vessels on the dynamic and post-gadolinium images. The standard deviation of the aorta signal was recorded as noise. Differences in the aorta and IVC signal-to-noise ratio were evaluated for each patient as well as for the means of all patients with Students t-test. In addition, the significance of differences in the mean portal vein, hepatic vein, renal vein and iliac vein signal compared to the IVC were evaluated with Students t-test. The presence of aneurysms, occlusions and stenoses (>50%) was noted on the individual dynamic images and on maximum intensity projections and compared to findings at surgery or arteriography when available.

Results:

All sixteen patients tolerated the imaging and gadopentetate dimeglumine well; there were no complications. FIGS. 8A–C illustrate the typical images obtained before, during and after injection of gadopentetate dimeglumine, respectively. Before the injection, the vessels were heavily saturated with only a few streaks of vessels visible at the edges of the 3D volume. Images obtained during injection showed enhancement of the arteries while the IVC remained indistinguishable from the background tissue. Aorta IVC signal intensity ratios, shown in TABLE 2, confirmed this preferential arterial enhancement in every patient studied. Images obtained after the injection was completed demonstrated comparable enhancement of both arteries and veins.

It should be noted that with dynamic imaging there is bright arterial as well as portal vein and splenic vein enhancement but no visible IVC or iliac vein enhancement and no in-plane saturation. Post gadopentetate dimeglumine images show comparable enhancement of both arteries and veins.

TABLE 3 provides the average signal intensity for all tissues studied for both the dynamic and post-injection sequences. With dynamic gadopentetate dimeglumine the average aorta signal-to-noise ratio was 10±0.9 compared to 5.1±1.4 in the IVC (p value≦0.0001), while post gadopentetate dimeglumine the aorta and IVC were nearly identical, 10±1.4 and 9.5±1.3 respectively. Although all veins were less bright than the aorta on the dynamic images compared to post gadopentetate dimeglumine images, there were variations among the veins analyzed. The iliac vein was the least enhanced, 4.7±1.6, while the portal vein was the brightest, 8.3±1.6 followed by the hepatic, 7.5±2.1, and renal, 6.2±1.8, veins; these differences were significant to the p<0.01 level compared to the mean IVC signal-to-noise ratio.

Angiographic and/or surgical correlation was available in 6 of the 16 patients. In the vascular segments for which definitive correlation was available, magnetic resonance arteriography correctly identified 2 occlusions (1 common iliac and 1 renal artery), 10 stenoses (4 renal artery, 2 iliac artery, 2 distal aorta, 1 inferior mesenteric artery and 1 celiac) and 6 aneurysms (3 aortic and 3 iliac artery). There was no evidence of arterial in-plane saturation in any patient. In one patient with a common iliac artery occlusion, there was no difficulty visualizing reconstituted flow distal to the occlusion.

TABLE 4 reveals an apparent trend for patients with a history of cardiac disease, claudication or aneurysms to have the greatest aorta/IVC signal intensity ratio. The sample size may have been too small to establish statistically significant correlations. Further, one patient with cardiac disease, aneurysmal disease and claudication had the highest aorta/IVC signal intensity ratio. These trends are opposite from time-of-flight imaging where cardiac disease and aneurysms are associated with image degradation.

EXAMPLE 2

In order to determine the optimal timing of contrast administration, two methods of dynamic administration, bolus and continuous infusion, were compared to non-dynamic injections and to conventional time-of-flight imaging.

Gadolinium enhanced magnetic resonance arteriography was performed in 52 patients referred for routine MRA of the abdominal aorta or branch vessels. Imaging was performed as described in Example 1. The total acquisition time was 5:08 minutes to cover approximately 36 cm of aorta and iliac artery in the superior to inferior dimension. In 20 of these patients, the dynamic gadolinium infusion imaging was performed with 28 partitions each 2 mm thick with a 256 by 256 matrix to reduce the scan time to 3:18 minutes.

After pre-scanning, venous access was obtained via a 22 gauge angiocatheter. A dynamic acquisition was then performed during hand injection of gadopentetate dimeglumine (Berlex Laboratories, Cedar Knoll, N.J.) 0.2 millimoles/Kg. In 12 patients, the injection was given as a bolus. The bolus was begun within 5 seconds of starting the acquisition and completed within the first 1 to 2 minutes of the 5 minute scan. In the other 40 patients, an injection of the same dose was carefully timed to be constant and continuous over the entire period of imaging beginning within 5 seconds of commencing the acquisition and ending 20 seconds before the end of the acquisition. In all patients, a 5 cc normal saline chaser was given to ensure injection of the entire gadopentetate dimeglumine dose.

For comparison purposes, 16 of these patients were imaged with an identical acquisition after the dynamic infusion without altering the imaging or prescan parameters. Also, for comparison, axial 2D and multiple overlapping 3D (MOTSA) time-of-flight images were acquired prior to the gadolinium injection. Inferior pre-saturation pulses were used with the time-of-flight sequences to suppress venous in-flow.

Signal intensity was measured in all patients in the aorta, IVC and background tissues (fat and skeletal muscle) for at least 3 regions of interest per measurement for all sequences. The signal's standard deviation within the aorta was recorded as noise.

Images obtained dynamically, during steady infusion of gadopentetate dimeglumine, showed sufficient arterial enhancement to clearly define the aorta and branch vessel anatomy while the IVC and iliac veins remained indistinguishable from the background tissues. The portal vein is visible but is not as bright as the aorta. Images obtained non-dynamically, after the injection was completed, or with a dynamic bolus injection demonstrated comparable enhancement of both arteries and veins.

Figure 9:
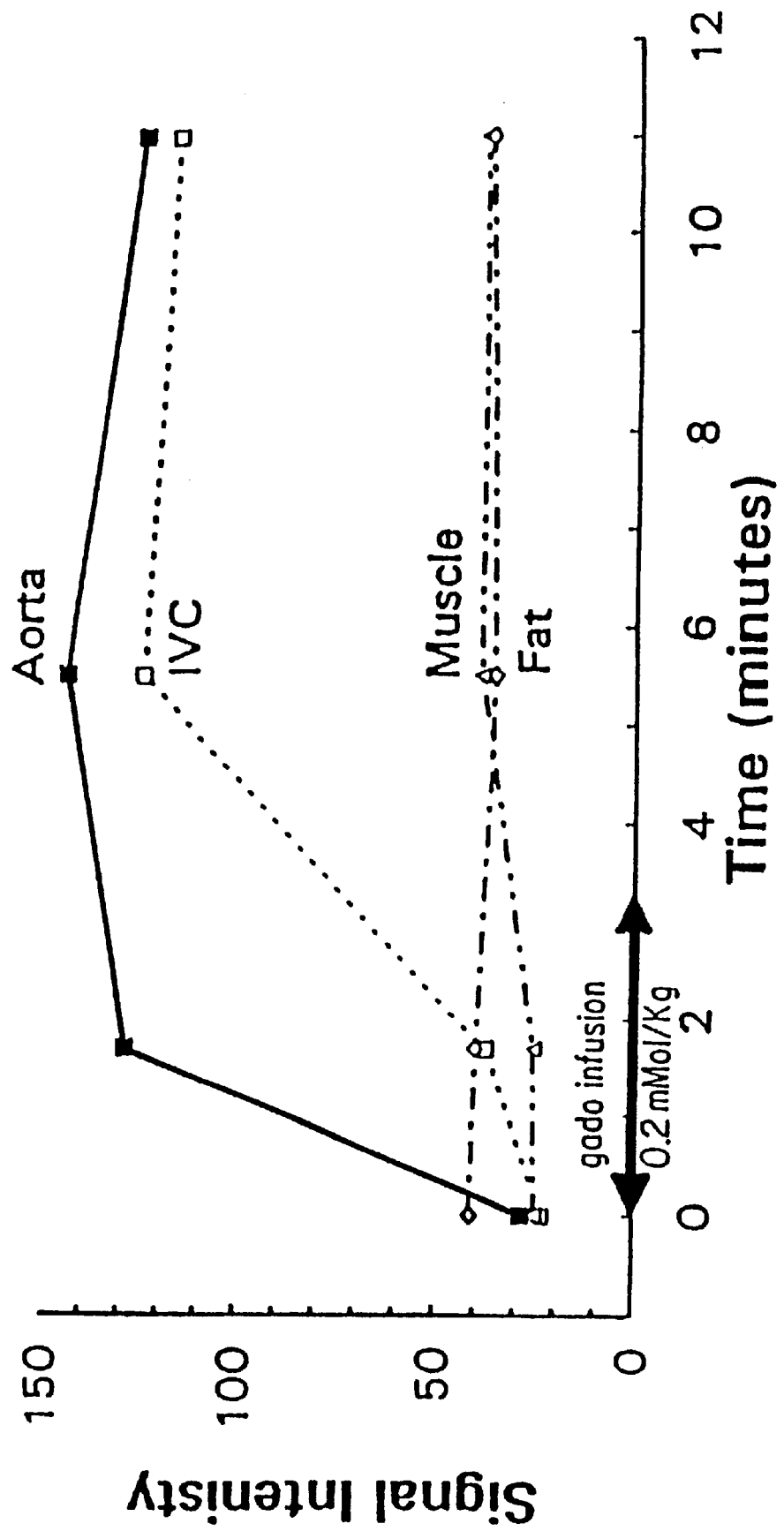
FIG. 9 illustrates region of interest analysis averaged for 3 patients who had pre-infusion, dynamic infusion, immediate post infusion and delayed 3D FT imaging. This figure shows that there is a short window, during contrast infusion, when the aorta signal intensity (solid squares) is higher than that of the IVC (open squares) and background tissues, fat (diamonds) and muscle (triangles)

The observation of significant, preferential arterial enhancement with a continuous dynamic contrast infusion was confirmed by region of interest analysis (see TABLE 5 and FIG. 9). The ratio of aorta to IVC signal intensity for the 5 minute infusion, 2.0±0.5, was significantly higher than for non-dynamic imaging 1.1±0.1 (p<0.001) or for the dynamic bolus 1.2±0.2 (p<0.001). Even better differentiation between the aorta and IVC was obtained by injecting the same dose of gadopentetate dimeglumine more quickly over a 3:18 minute acquisition. Although this aorta-to-IVC signal intensity ratio was not as favorable as for 2D time-of-flight or MOTSA imaging, it was adequate in all cases for clearly distinguishing the aorta and abdominal aorta branch vessels from the IVC and iliac veins.

Dynamic contrast enhanced 3D imaging had no saturation, pulsatility or misregistration artifacts. Even in aneurysms, which tend to have stagnant and/or turbulent flow, there was no loss of signal. By comparison, every 2D time-of-flight study had pulsatility artifacts and some had misregistration and/or in-plane saturation artifacts. The MOTSA images had no pulsatility or misregistration artifacts but every MOTSA study showed some degree of arterial saturation and they were particularly degraded in aneurysmal segments.

Administering gadopentetate dimeglumine dynamically as a steady, continuous, infusion for the entire period of a 3D FT acquisition, at a dose of 0.2 millimoles/Kg, gives sufficient preferential arterial enhancement to visualize arteries distinctly from veins and background tissues regardless of the magnitude or direction of flow. The importance of injecting dynamically and continuously during the entire scan is illustrated by the absence of significant preferential enhancement when the contrast is administered non-dynamically or as a dynamic bolus. Images obtained at a lower dose, 0.1 millimole/Kg, were not useful.

Since dynamic gadolinium enhanced MRA does not depend upon the in-flow of unsaturated spins, it eliminates some of the saturation problems that complicate routine time-of-flight imaging. The imaging volume can be oriented in any plane for optimal coverage of the vessels of interest without concern for saturation. In these patients, in-plane, coronal imaging of the aorta-iliac system reduced the image acquisition time by 5 to 20 fold over 2D time-of-flight and MOTSA imaging and had superior resolution and superior aorta signal-to-noise ratios.

A 3D FT acquisition was used in this example partly because of its intrinsically high spatial resolution and high signal-to-noise and also because its main limitation, arterial saturation, is eliminated by the gadolinium. The TE was chosen to be as short as possible at a value where fat and water protons are out of phase. A short TE helps to minimize motion related phase artifacts. Having fat and water out of phase provides an element of fat suppression which improves artery-to-background contrast since fat is the brightest background tissue.

EXAMPLE 3

MRA image data for a patient presenting with an abdominal aortic aneurysm was acquired as described in Example 1. MRA images are shown in FIGS. 10A and 10B.

Figure 10A:
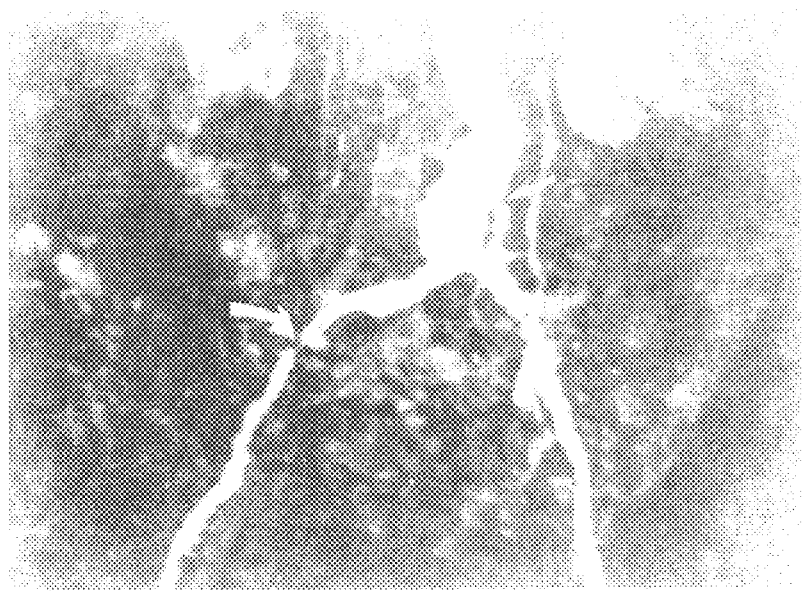
FIG. 10A is an illustrative example of a magnetic resonance image of a patient with an abdominal aortic aneurysm. The magnetic resonance angiography ("MRA") depicts the aneurysmal aorta and aneurysmal common iliac arteries as well as severe stenoses of the right external iliac (curved arrow) and inferior mesenteric (straight arrow) arteries and a mild stenosis of the left common iliac artery.
Figure 10B:
FIG. 10B illustrates a digital subtraction angiogram of the aneurysmal aorta and aneurysmal common iliac arteries as well as severe stenoses of the right external iliac (curved arrow) and inferior mesenteric (straight arrow) arteries and a mild stenosis of the left common iliac artery of FIG. 10A.

The MRA of FIG. 10A depicts the aneurysmal aorta and aneurysmal common iliac arteries as well as severe stenoses of the right external iliac (curved arrow) and inferior mesenteric (straight arrow) arteries and a mild stenosis of the left common iliac artery. The internal iliac arteries are excluded because of their posterior course. FIG. 10B illustrates a digital subtraction angiogram which confirms the findings in FIG. 10A as discussed immediately above.

EXAMPLE 4

A pump (as illustrated in FIG. 5A) was loaded with a 50 cc syringe containing 42 cc of gadodiamide. A 23 gauge butterfly was attached to the end of the syringe with its standard luer-lock connector and plugged into a side port of the patient's intravenous (IV) line within a few feet of the IV skin entry site. The pump was located approximately 15 cm or more away from the imaged volume.

Usually the IV site was in the forearm or antecubital fossa. A plastic Kelly clamp on the butterfly tubing prevented premature gadolinium infusion. The gadolinium infusion was begun simultaneous with beginning the image acquisition by releasing the clamp on the butterfly tubing. This combination of 6 pounds spring force and a ⅝ inch, 23 gauge butterfly needle gave an infusion rate of 18 cc/minute which was slightly reduced by the additional resistance of the IV tubing and angiocatheter. For the 42 cc volume of gadolinium, the calculated infusion time was 2:20 minutes. This was shortened by manually increasing the rate of injection during the middle of the acquisition such that the maximum arterial concentration occurred during acquisition of the center of k-space.

The pump infusion finished with one minute of scan time remaining. Residual gadolinium within the IV tubing (about 4 cc) was flushed through with saline to ensure delivery of the entire dose.

The procedure of EXAMPLE 4 produced excellent quality MRA images of arteries without the confounding effects of excessive venous enhancement.

EXAMPLE 5

By way of overview, anatomic data defined by magnetic resonance imaging, including abdominal aortic aneurysm size and character as well as the status of the celiac, mesenteric, renal and iliac arteries, were examined in 43 patients. Five magnetic resonance sequences used in examining these patients. The five magnetic resonance sequences were obtained in about an hour-long is exam optimized for aortoiliac, splanchnic and renal artery imaging at 1.5 Tesla in a body coil. Four of the sequences were performed during or following infusion of gadolinium to improve image quality.

Imaging was performed on a 1.5 Tesla Magnet (GE Medical Systems, Signa, Milwaukee, Wis.) using the body coil. The imaging sequences included Sagittal T1 (9:36 minutes), Coronal 3D spoiled gradient echo during infusion of 42 or 63 ml gadolinium chelate (3:20 minutes), Sagittal 2D time-of-flight (4 minutes), Axial 2D time-of-flight (10 minutes), and Axial 3D phase contrast (13:07 minutes) images. Each sequence was performed using the GE Signa Magnet, 1.5 Tesla with 5.3 software. The imaging parameters, details regarding the gadolinium infusion rate and timing, and methods of image reconstruction are described in more detail below.

Magnetic resonance images were independently analyzed by two vascular radiologists blinded to the findings at angiography, surgery, and computed tomography. Any disagreements in interpretation were resolved by consensus. Aneurysms were classified as suprarenal (aneurysmal above the renal arteries) pararenal (aneurysm at level of renal arteries but not higher), juxtarenal (origin of aneurysm at or within 1 cm below renal arteries) or infrarenal (origin of aneurysm more than 1 cm below renal arteries). (See TABLE 6). The distal extent was defined as the first point inferior to the aneurysm that was near-normal caliber. The maximum aneurysm diameter was measured electronically on the MR computer monitor from its outer-to-outer wall margins. Thrombus, when present, was noted. The celiac, proximal superior mesenteric, renal, common iliac, external iliac, and internal iliac arteries were graded as normal, mildly diseased (less than 50%), moderately stenotic (50–75%), severely stenotic (greater than 75%) or occluded.

Magnetic resonance images were also evaluated for evidence of aortic dissection, inflammatory changes and aortic rupture. Aortic dissection may be defined as an aorta having an intimal flap or medial separation. Inflammatory aneurysm may be defined as having surrounding enhancing tissue. Ruptured aneurysm may be defined as having an aortic mural defect and a retroperitoneal collection with magnetic resonance features of hemorrhage.

The imaging parameter details are described below in a form compatible with the GE Signa Magnet, 1.5 Tesla with 5.3 software. Those parameters, however, may be converted or extrapolated for use with other imaging systems; and, as a result, they are exemplary in nature.

An initial sagittal T1-weighted spin echo localizer was landmarked just below the xyphoid and obtained using the following parameters: TR=333 msec, TE=25 msec, bandwidth=16 kHz, slice thickness=8 mm (performed as a triple interleave with no gap), respiratory compensation, matrix=256 by 128 pixels with frequency encoding superior to inferior, a 40–48 cm field of view and 2 NEX. Image acquisition time was 9:35 minutes.

A first gadolinium-enhanced acquisition was a coronal 3D spoiled gradient echo sequence centered on the abdominal aorta and obtained with the following parameters: TR=24 msec, TE=6.9 msec, flip angle=40 degrees, bandwidth=16 kHz, 28 slices with 2.5 to 2.8 mm slice thickness, matrix=256 by 256 pixels, frequency encoding superior to inferior, first order gradient moment nulling (flow compensation), field-of-view=36 cm, 1 NEX. No saturation pulses were employed; the total image acquisition time was 3:20 minutes.

The coronal volume was positioned with the top edge at the diaphragm just below the heart and the front edge anterior to the pre-aortic left renal vein where it passed under the superior mesenteric artery and anterior to the common femoral arteries at the level of the femoral heads. If the posterior edge of the volume did not reach back into the renal parenchyma bilaterally, the slices were made thicker up to a maximum thickness of 2.8 mm. In most cases, this 28 slice coronal volume was too thin to image the entire aneurysm; accordingly the anterior margin of the aneurysm was deliberately excluded on this sequence.

Gadolinium was infused during the acquisition in order to preferentially enhance arteries more than veins. The same volume, 42 ml (two vials, 21 mMol), Gadodiamide (Omniscan; Sanofi Winthrop Pharmaceuticals, New York, N.Y.), Gadoteridol (ProHance; Squibb Diagnostics, Princeton, N.J.) or Gadopentetate Dimeglumine (Magnevist; Berlex Laboratories, Wayne, N.J.) was used in every patient under 95 Kg (210 pounds). Patients weighing greater than 95 Kg were given three vials (63 ml) of gadolinium. The gadolinium infusion was begun simultaneously with image acquisition using an MR compatible infusion pump (Reddington Medical Technologies, Inc. East Walpole, Mass.) The infusion was completed 60 seconds prior to scan termination including a 10 to 20 ml saline flush. This saline flush was given to ensure delivery of the entire dose of contrast. Special care was taken to maintain a high infusion rate during the middle of the acquisition when the center of k-space was acquired.

Immediately following the dynamic gadolinium acquisition, 6 to 8 contiguous, sagittal 2D time-of-flight, spoiled, gradient echo At images were acquired, centered on the visceral arteries with the following parameters: TR=33, TE=minimum (7 msec), flip angle=45 degrees, bandwidth=16 kHz, slice thickness=6 cm, first order gradient moment nulling (flow compensation), matrix=256 by 192, frequency encoding superior-to-inferior, 36 cm field-of-view, 1 NEX. Each sagittal image was obtained during suspended respiration (7 seconds per breath hold). Immediately following these sagittal images, axial 2D time-of-flight gradient echo images were obtained in a similar fashion with the following parameters: TR=22 msec, TE=minimum full (12 msec), flip angle=60 degrees, bandwidth=16 kHz, slice thickness=8 mm with a 5 mm interslice gap, matrix=256 by 256, 28 to 32 cm field-of-view, first order gradient moment nulling (flow compensation), and no phase wrap. The axial images covered from above the celiac trunk to below the AAA. If the iliac arteries were aneurysmal, the axial 2D time-of-flight images were extended down into the pelvis. The acquisition was performed either with 2 averages (NEX) and suspended respiration or with 4 averages and phase reordering with respiration (respiratory compensation).

Following the time-of-flight images (sagittal and axial 2D time-of-flight images), an axial 3D phase contrast volume was acquired centered on the renal arteries with the following parameters: TR=24 msec, TE=7.7 msec, flip angle=45 degrees, bandwidth=16 kHz, field-of-view=32 cm, 28 slices with 2.5 mm slice thickness, flow compensation, no phase wrap, matrix=256 by 128, frequency encoding right-left, 32 cm field-of-view, 2 NEX with velocity encoding in all directions at 30 cm/sec. The image acquisition time was 13:07 minutes. Images were reconstructed with the phase difference method illustrating maximum velocity in all flow directions as well as right-to-left flow to evaluate the retrocaval course of the right renal artery. In patients suspected of having very slow renal artery flow, such as patients with a serum creatinine greater than 3 mg/dl, the velocity encoding was reduced to 20 cm/sec.

Images were reconstructed by a vascular radiologist using a computer workstation (GE Medical Systems, Milwaukee, Wis.). Subvolume maximum intensity projections and single voxel thick reformations were made through the origins of each of the major aortic branch vessels. The subvolume maximum intensity projections were made by reviewing the raw data images to identify the minimum number of images required to demonstrate the renal arteries and then collapsing these into a single coronal image. This was similarly performed for the aorto-iliac system. A sagittal subvolume maximum intensity projection was performed centered on the celiac and superior mesenteric arteries for both the dynamic gadolinium-enhanced coronal sequence and for the sagittal 2D time-of-flight sequence.

EXAMPLE 6

Twenty-five patients were imaged with a shortened 3D spoiled gradient echo acquisition that could be performed during suspension of respiration. To shorten the acquisition time to under 1 minute, the TR was reduced to 14 msec and the TE was reduced to 2.6 msec. A 28 slice 3D volume with a 256 by 128 matrix required a 58 second breath-hold and a 12 slice volume required a 29 second breath-hold.

Gadolinium was infused intravenously as a 30 second bolus beginning approximately 40 to 50 seconds before the middle of the image acquisition. In this way, the arterial gadolinium concentration was expected to be maximum during the middle of the acquisition when data representative of the center of k-space was acquired.

It should be noted that for short scans (i.e., less than 1 to 2 minutes) one manner of calculating a scan time delay (i.e., a delay between the beginning of imaging and the beginning of infusion) more accurately is to employ the following relationship:

Scan Time Delay=Estimated circulation time+(infusion time/2)−(imaging time/2)

The estimated circulation time is the time required for contrast to travel from the site of injection/infusion to the artery of interest; the infusion time is the time duration of the contrast infusion; and the imaging time is the time duration of the image acquisition. The relationship defined above assumes that the data representative of the center of k-space is acquired in the middle of the image acquisition. In those instances where data corresponding to the center of k-space is collected at a time other than during the middle of the acquisition, the relationship may be adjusted accordingly.

In all patients who were able to cooperate with breath-holding, the renal arteries were well seen all the way to the renal hilum. In two patients who could not cooperate with breath-holding there was degradation (blurring) of the distal renal artery making it more difficult to evaluate.

Various preferred embodiments of the present invention have been described. It is understood, however, that changes, modifications and permutations can be made without departing from the true scope and spirit of the present invention as defined by the following claims, which are to be interpreted in view of the foregoing.

For example, many different combinations may be employed in providing anatomic images of the abdominal aorta. Under some circumstances when imaging abdominal aortic aneurysms, not all sequences are necessary to provide sufficient images and/or information of the aneurysm. An imaging technique using several of the sequences may provide limited information of, for example, the distal end of the aneurysm (dynamic gadolinium enhanced 3D volume imaging sequence) and the maximum size of the aneurysm (sagittal and axial 2D time-of-flight images). One skilled in the art would recognize that other permutations of the sequences are possible and the number and combination of the sequences may be tailored according to the information needed or desired.

Further, several of the sequences may be repeated in order to collect additional, but somewhat cumulative information. A sequence may be performed more than once in order to check the imaging results from other sequences. Thus, in short, numerous permutations of sequences may be implemented to provide varying degrees of evaluation, as well as certainty, of abdominal aortic aneurysms.

Moreover, when performing those sequences that employ a magnetic resonance contrast agent, the correlation techniques for adapting the timing of a maximum or elevated rate of infusion and the collection of image data representative of the center of k-space may be used in various combinations according to the particulars of the contrast delivery system, the artery of interest, the location of the artery of interest, the size of the artery of interest, the condition of the patient, and the type of pulse sequence employed by the imaging apparatus. Adapting the timing of a maximum or elevated rate of infusion to correlate with the collection of image data representative of the center of k-space insures that such data will be collected over some period during which a maximum or elevated contrast concentration is realized in the artery of interest.

Infusion Rates of Gadolinium Chelates at 24° C.

TABLE 1

| Flow Restrictor | Size | Infusion Rate | | |
|---|---|---|---|---|
| | | Gd-DTPA | Gadoteridol | Gadodiamide |
| Viscosity @ 20° C. [cP]* | | 4.9 | 2.0 | 2.0 |
| Needles | | | | |
| BD ® | 18 g 1.5" | 100 | 126 | 120 |
| Terumo ® | 20 g 1.5" | 44 | 66 | 64 |
| Terumo ® | 21 g 1.5" | 27 | 47 | 44 |
| Terumo ® | 22 g 1.5" | 15 | 29 | 23 |
| Terumo ® | 23 g 1" | <4 | <4 | <4 |
| Butterflies | | | | |
| ABBOTT ® | 21 g .75" | 21 | 37 | 36 |
| ABBOTT ® | 23 g .75" | 8 | 19 | 18 |
| ABBOTT ® | 25 g .375" | <4 | 8 | 7.3 |
| Orifice | | | | |
| | 0.010" | 21 | 25 | 25 |

*Values provided by manufacturer (Nycomed)

TABLE 2

Aorta/IVC Signal Intensity Ratios for Dynamic 3D Imaging

| Patient #-sex | Age | Primary Indication | Heart Disease | Creatinine | Signal Intensity During Injection | | | |
|---|---|---|---|---|---|---|---|---|
| | | | | | Aorta | IVC | ratio** | p value |
| 1-m | 83 | AAA | yes* | 2 | 7.9 ± 1.0 | 3.9 ± 0.6 | 2.0 | <.0001 |
| 2-f | 73 | hypertension | yes* | .8 | 11 ± 1.0 | 8.2 ± 1.3 | 1.4 | .0002 |
| 3-m | 73 | claudication | yes | 2.2 | 10 ± 2.0 | 3.7 ± 0.5 | 2.8 | .0003 |
| 4-f | 67 | hypertension | no | .9 | 10 ± 0.4 | 5.1 ± 0.6 | 2.0 | <.0001 |
| 5-f | 70 | hypertension | yes* | 3 | 8.9 ± 0.9 | 4.5 ± 0.4 | 2.0 | <.0001 |
| 6-m | 67 | renal failure | yes | 6 | 11 ± 0.5 | 4.9 ± 0.4 | 2.2 | <.0001 |
| 7-f | 80 | AAA | yes | 1.8 | 10 ± 0.4 | 5.9 ± 0.5 | 1.8 | <.0001 |
| 8-f | 76 | renal failure | yes* | 3.6 | 9.1 ± 0.6 | 5.0 ± 0.6 | 1.8 | <.0001 |
| 9-m | 68 | AAA | no | 1 | 11 ± 0.5 | 7.2 ± 0.3 | 1.4 | <.0001 |
| 10-m | 70 | claudication | yes | 1.2 | 11 ± 0.5 | 5.4 ± 0.3 | 2.0 | <.0001 |
| 11-m | 74 | hypertension | no | 1 | 8.9 ± 0.3 | 6.0 ± 0.8 | 1.5 | <.0001 |
| 12-m | 80 | hypertension | yes* | 3.2 | 10 ± 0.4 | 3.8 ± 0.9 | 2.6 | <.0001 |
| 13-m | 74 | AAA | yes | 4 | 9.8 ± 1.0 | 3.7 ± 0.8 | 2.6 | <.0001 |
| 14-f | 67 | AAA | no | 1 | 10 ± 0.3 | 5.9 ± 0.6 | 1.8 | <.0001 |
| 15-m | 67 | hypertension | no | 1.5 | 11 ± 0.9 | 4.6 ± 0.9 | 2.4 | <.0001 |
| 16-f | 71 | claudication | yes* | 6 | 11 ± 1.3 | 3.1 ± 0.6 | 3.5 | <.0001 |
| | | AVERAGE | | | 10 ± 0.9 | 5.1 ± 1.4 | 2.0 | <.0001 |

*cardiac disease with history of CHF
**Aorta/IVC signal intensity ratio

TABLE 3

Average Signal-To-Noise Ratios
During and Post Gadopentetate Dimeglumine Injection

|  | Dynamic Injection | Post Injection | Ratio Dynamic/Post |
|---|---|---|---|
| ARTERIES | | | |
| Aorta | 10 ± 0.9 | 10 ± 1.4 | 1.0 |
| Iliac Artery | 9.8 ± 1.3 | 10 ± 1.3 | .98 |
| Renal Artery | 9.7 ± 1.9 | 10 ± 2.5 | .99 |
| Celiac & SMA | 10 ± 1.7 | 11 ± 1.8 | .91 |
| VEINS | | | |
| IVC | 5.1 ± 1.4 | 9.5 ± 1.3** | .54 |
| Iliac Vein | 4.7 ± 1.6* | 9.2 ± 1.3** | .51 |
| Renal Vein | 6.2 ± 1.8* | 9.1 ± 1.9** | .68 |
| Hepatic Vein | 7.5 ± 2.1* | 8.3 ± 1.0** | .90 |
| Portal Vein | 8.3 ± 1.6* | 9.0 ± 3.3** | .92 |
| BACKGROUND | | | |
| Kidney | 7.3 ± 1.0 | 8.3 ± 1.0 | .88 |
| Liver | 5.3 ± 0.6 | 5.8 ± 1.8 | .91 |
| Spleen | 5.9 ± 2.3 | 6.3 ± 2.3 | 1.1 |
| Fat | 4.3 ± 0.7 | 4.0 ± 0.8 | 1.1 |
| Muscle | 2.4 ± 0.5 | 3.2 ± 0.7 | .75 |

*$p > 0.01$ compared to IVC signal intensity
**$p > 0.01$ compared to signal intensity for dynamic injection
***standard deviation of signal in the space outside the patient

TABLE 4

Effect of Cardiac Disease, Claudication and
Aneurysms on Aorta/IVC Signal Intensity Ratio

| Subgroup | # of Patients | Aorta/IVC* | p value |
|---|---|---|---|
| Cardiac Disease | 12 | 2.2 ± 0.6 | 0.08 |
| No Cardiac Disease | 4 | 1.8 ± 0.4 | 0.08 |
| Claudication | 4 | 2.6 ± 0.8 | 0.12 |
| No Claudication | 12 | 2.0 ± 0.4 | 0.12 |
| Aneurysm | 7 | 2.2 ± 0.7 | 0.32 |
| No Aneurysm | 9 | 2.0 ± 0.5 | 0.32 |

*Signal Intensity Ratio

TABLE 6

Characteristics of Abdominal Aortic Aneurysms

| | |
|---|---|
| Suprarenal | 11 |
| Pararenal | 6 |
| Juxtarenal | 6 |
| Infrarenal | 20 |
| Mean Diameter (min–max) | 5.4 (3–8.7) cm |
| Thrombus | 35 (81%) |
| Inflammatory AAA | 1 (2%) |
| Leaking AAA | 1 (2%) |
| Retro-Aortic Renal Vein | 6 (14%) |
| Accessory Renal Arteries | 5 (12%) |

TABLE 5

Effect of Injection Method on
Aorta Signal-to-Noise and Contrast-to-Noise Ratios

| Pulse Sequence | Contrast Injection Method | # of patients | Image time/cm (sec/cm) | Voxel Volume (mm³) | Saturation Artifacts | Pulsatility Artifacts | Aorta SNR | Aorta/IVC SI ratio | Aorta-IVC CNR | Aorta-fat CNR | Aorta-muscle CNR |
|---|---|---|---|---|---|---|---|---|---|---|---|
| 2D TOF | No gado | 11 | 40 | 6.0 | yes | yes | 8.2 ± 2.8 | 3.7 ± 1 | 5.8 ± 1.9 | 5.5 ± 2 | 6.8 ± 2.4 |
| MOTSA | No gado | 12 | 92 | 4.7 | yes | no | 8.9 ± 2.5 | 2.7 ± 0.9 | 5.1 ± 1.8 | 4.9 ± 1.7 | 6.3 ± 1.9 |
| Gado: 3D | non-dynamic | 16 | 9 | 3.1 | no | no | 9 ± 2.0 | 1.1 ± 0.1 | 0.6 ± 0.5 | 5.4 ± 1.5 | 6.2 ± 1.9 |
| Gado: 3D | bolus* | 12 | 9 | 3.1 | no | no | 12 ± 2.4 | 1.2 ± 0.2 | 2.7 ± 1.4 | 7.5 ± 1.6 | 9.1 ± 1.9 |
| Gado: 3D | infusion**[1] | 20 | 9 | 3.1 | no | no | 10 ± 1.2 | 2.0 ± 0.5 | 4.7 ± 1.4 | 5.4 ± 1.1 | 7.3 ± 1.1 |
| Gado: 3D | infusion**[2] | 20 | 5.5 | 3.1 | no | no | 10 ± 2 | 2.4 ± 0.8 | 5.6 ± 1.7 | 6.8 ± 1.9 | 8.2 ± 1.7 |

SNR = signal-to-noise ratio
CNR = contrast-to-noise ratio
*gadopentetate dimeglumine given dynamically as a bolus within the first 2 minutes of the acquisition.
**gadopentetate dimeglumine given dynamically as a constant infusion spread over the entire acquisition.
[1] 5 minutes
[2] 3 minutes

What is claimed is:

1. A method of imaging a portion of the aorta of a patient using a magnetic resonance imaging system, the method comprising:
   determining an arrival time of a test bolus in a region of interest;
   correlating an administration of a magnetic resonance contrast agent with an acquisition of magnetic resonance image data using the arrival time of the test bolus;
   administering the magnetic resonance contrast agent to the patient; and
   acquiring the magnetic resonance image data using a 3D pulse sequence having a TR which is less than about 25 milliseconds, a TE which is less than about 7 milliseconds, and a slice thickness of less than about 4 millimeters, wherein the image data is acquired while the concentration of the contrast agent in the portion of the aorta is greater than a concentration of the contrast agent in veins and background tissue adjacent to the portion of the aorta.

2. The method of claim 1 wherein acquiring magnetic resonance image data further includes using a flip angle which is greater than about 30° and less than or equal to about 90°.

3. The method of claim 1 wherein acquiring magnetic resonance image data further includes using a TR which is less than about 10 milliseconds and a TE which is less than about 3 milliseconds.

4. The method of claim 1 wherein acquiring magnetic resonance image data further includes acquiring a substantial portion of the image data while the patient suspends respiration.

5. The method of claim 1 further including:
correlating the acquisition of magnetic resonance image data which is representative of the center of k-space with the administration of the magnetic resonance contrast agent.

6. The method of claim 1 wherein acquiring magnetic resonance image data further includes using a 3D spoiled gradient echo pulse sequence.

7. The method of claim 1 further including imaging at least one renal artery of the patient by acquiring magnetic resonance image data, of a coronally oriented image volume including the renal artery, using a gradient echo pulse sequence, the image data being acquired while the concentration of the contrast agent in the renal artery is substantially greater than a concentration of the contrast agent in veins and background tissue adjacent to the artery.

8. The method of claim 1 further including imaging at least one renal artery of the patient by acquiring magnetic resonance image data including image data which is representative of the center of k-space while the concentration of the contrast agent in the renal artery is substantially greater than a concentration of the contrast agent in veins and background tissue adjacent to the artery.

9. The method of claim 8 wherein imaging at least one renal artery of the patient further includes collecting 3D phase contrast images.

10. The method of claim 1 wherein the image volume of the 3D pulse sequence includes at least one dimension which is greater than 25 centimeters.

11. The method of claim 1 further including:
collecting image data of a pre-contrast image data set including collecting image data before administering a substantial amount of the magnetic resonance contrast agent to the patient; and
constructing an image of the portion of the aorta by subtracting the image data of the pre-contrast image data set from the image data acquired while the concentration of the contrast agent in the portion of the aorta is greater than a concentration of the contrast agent in veins and background tissue adjacent to the portion of the aorta.

12. The method of claim 1 wherein administering the magnetic resonance contrast agent to the patient includes infusing the contrast agent to the patient at a rate which is greater than 0.0015 liters/kilogram-second2 divided by the relaxivity of the contrast agent.

13. The method of claim 1 further including:
acquiring image data of the periphery of k-space while the concentration of the contrast agent in the aorta is greater than a concentration of the contrast agent in veins and background tissue adjacent to the aorta.

14. The method of claim 1 wherein collecting magnetic resonance image data includes acquiring image data which is representative of the periphery of k-space immediately after acquiring image data which is representative of the center of k-space.

15. The method of claim 1 wherein collecting magnetic resonance image data includes collecting image data which is representative of a first portion of the periphery of k-space immediately before collecting image data which is representative of the center of k-space and collecting image data which is representative of a second portion of the periphery of k-space immediately after collecting image data which is representative of the center of k-space.

16. A method of imaging an abdominal aorta of a patient using a magnetic resonance imaging system, the method comprising:
determining an arrival time of a magnetic resonance contrast agent in a region of interest;
correlating an administration of the magnetic resonance contrast agent to the patient with a collection of magnetic resonance image data using the arrival time of the magnetic resonance contrast agent in the region of interest;
administering the magnetic resonance contrast agent to the patient; and
collecting the magnetic resonance image data using 3D pulse sequence, wherein collecting magnetic resonance image data includes collecting a substantial portion of the image data while the concentration of the contrast agent in the abdominal aorta is greater than a concentration of the contrast agent in veins and background tissue adjacent to the abdominal aorta.

17. The method of claim 16 wherein the arrival time of the magnetic resonance contrast agent is an estimated arrival time.

18. The method of claim 16 further including correlating collection of magnetic resonance image data which is representative of the center of k-space with the arrival time of the contrast agent in the region of interest.

19. The method of claim 16 wherein determining the arrival time of a magnetic resonance contrast agent in the region of interest includes using a test bolus.

20. The method of claim 16 wherein collecting magnetic resonance image data includes collecting a substantial portion of the image data which is representative of the center k-space while the patient suspends respiration.

21. The method of claim 16 wherein collecting magnetic resonance image data further includes using a TR which is less than about 25 milliseconds and a TE which is less than about 7 milliseconds.

22. The method of claim 16 wherein collecting magnetic resonance image data further includes using a TR which is less than about 10 milliseconds, a TE which is less than about 7 milliseconds, and a flip angle which is between about 30° and about 90°.

23. The method of claim 16 wherein collecting magnetic resonance image data further includes using a TE which is less than about 3 milliseconds and a flip angle which is at least about 45°.

24. The method of claim 16 further including imaging at least one renal artery of the patient by collecting magnetic resonance image data using a 3D pulse sequence and coronally oriented image volume wherein the image volume includes at least a portion of the renal artery, the image data being collected while the concentration of the contrast agent in the renal artery is greater than a concentration of the contrast agent in veins and background tissue adjacent to the artery.

25. The method of claim 16 further including imaging at least one renal artery of the patient by collecting image data which is representative of the center of k-space while the concentration of the contrast agent in the renal artery is greater than a concentration of the contrast agent in veins and background tissue adjacent to the artery.

26. The method of claim 16 wherein collecting magnetic resonance image data further includes using a slice thickness which is less than about 4 millimeters and the image volume of the 3D pulse sequence includes at least one dimension which is at least about 25 centimeters.

27. The method of claim 16 further including:
collecting image data of a pre-contrast image data set including collecting image data before administering a substantial amount of the magnetic resonance contrast agent to the patient; and
constructing an image of the abdominal aorta by subtracting the image data of the pre-contrast image data set from the image data acquired while the concentration of the contrast agent in the abdominal aorta is substantially greater than a concentration of the contrast agent in veins and background tissue adjacent to the abdominal aorta.

28. The method of claim 16 wherein collecting magnetic resonance image data further includes collecting image data of the periphery of k-space while the concentration of the contrast agent in the aorta is greater than a concentration of the contrast agent in veins and background tissue adjacent to the aorta.

29. The method of claim 16 wherein administering the magnetic resonance contrast agent to the patient includes infusing the contrast agent to the patient at a rate which is greater than 0.0015 liters/kilogram-second$^2$ divided by the relaxivity of the contrast agent.

30. The method of claim 16 wherein determining the arrival time of a magnetic resonance contrast agent in the region of interest includes estimating the arrival time based on the physical condition or age of the patient.

31. The method of claim 16 wherein collecting magnetic resonance image data includes acquiring image data which is representative of the periphery of k-space immediately after acquiring image data which is representative of the center of k-space.

32. The method of claim 16 wherein collecting magnetic resonance image data includes acquiring image data which is representative of a first portion of the periphery of k-space immediately before collecting image data which is representative of the center of k-space and collecting image data which is representative of a second portion of the periphery of k-space immediately after collecting image data which is representative of the center of k-space.

33. A method of imaging an abdominal aorta of a patient using a magnetic resonance imaging system wherein the abdominal aorta is located in a region of interest, the method comprising:
calculating an arrival time of the contrast agent in the region of interest;
administering a magnetic resonance contrast agent to the patient; and
collecting magnetic resonance image data of an image volume, which includes the abdominal aorta, based on the arrival time and using a 3D pulse sequence having a TR which is less than about 25 milliseconds, a TE which is less than about 7 milliseconds, and a slice thickness of less than about 4 millimeters, wherein at least a portion of the image data is collected while the concentration of the contrast in the abdominal aorta is greater than a concentration of the contrast agent in veins and background tissue adjacent to the abdominal aorta.

34. The method of claim 33 wherein the collecting magnetic resonance image data includes using a body coil.

35. The method of claim 34 wherein calculating the arrival time of the contrast agent in a region of interest includes using a test bolus.

36. The method of claim 33 wherein collecting magnetic resonance image data further includes collecting image data which is representative of the center of k-space based on the arrival time.

37. The method of claim 33 wherein collecting magnetic resonance image data includes collecting a substantial portion of the image data while the patient suspends respiration.

38. The method of claim 33 wherein collecting magnetic resonance image data further includes using a TE which is less than about 3 milliseconds and TR which is less than about 10 milliseconds.

39. The method of claim 33 further including imaging at least one renal artery of the patient by collecting magnetic resonance image data using a 3D gradient echo pulse sequence, the image data being collected while the concentration of the contrast agent in the renal artery is greater than a concentration of the contrast agent in veins and background tissue adjacent to the renal artery.

40. The method of claim 33 wherein calculating the arrival time of a magnetic resonance contrast agent in the region of interest includes calculating the arrival time based on the physical condition or age of the patient.

41. The method of claim 33 further including:
collecting image data of a pre-contrast image data set including collecting image data before administering a substantial amount of the magnetic resonance contrast agent to the patient; and
constructing an image of the abdominal aorta by subtracting the image data of the pre-contrast image data set from the image data acquired while the concentration of the contrast agent in the abdominal aorta is substantially greater than a concentration of the contrast agent in veins and background tissue adjacent to the abdominal aorta.

42. The method of claim 33 wherein collecting magnetic resonance image data includes collecting image data of the periphery of k-space while the concentration of the contrast agent in the aorta is greater than concentration of the contrast agent in veins and background tissue adjacent to the aorta.

43. The method of claim 33 wherein collecting magnetic resonance image data includes collecting image data which is representative of the center of k-space while the patient suspends respiration.

44. The method of claim 33 wherein collecting magnetic resonance image data includes collecting image data which is representative of the periphery of k-space immediately after collecting image data which is representative of the center of k-space.

45. The method of claim 33 wherein collecting magnetic resonance image data includes collecting image data which is representative of a first portion of the periphery of k-space immediately before collecting image data which is representative of the center of k-space and collecting image data which is representative of a second portion of the periphery of k-space immediately after collecting image data which is representative of the center of k-space.

* * * * *